US009284567B2

(12) United States Patent
Hiei et al.

(10) Patent No.: US 9,284,567 B2
(45) Date of Patent: Mar. 15, 2016

(54) METHOD FOR GENE INTRODUCTION INTO HORDEUM PLANT USING AGROBACTERIUM, AND METHOD FOR PRODUCTION OF TRANSFORMED PLANT OF HORDEUM PLANT

(75) Inventors: Yukoh Hiei, Iwata (JP); Yuji Ishida, Iwata (JP)

(73) Assignee: JAPAN TOBACCO INC., Tokyo (JP)

( * ) Notice: Subject to any disclaimer, the term of this patent is extended or adjusted under 35 U.S.C. 154(b) by 403 days.

(21) Appl. No.: 13/812,412

(22) PCT Filed: Jul. 29, 2011

(86) PCT No.: PCT/JP2011/067493
§ 371 (c)(1),
(2), (4) Date: Jan. 25, 2013

(87) PCT Pub. No.: WO2012/015039
PCT Pub. Date: Feb. 2, 2012

(65) Prior Publication Data
US 2013/0125266 A1 May 16, 2013

(30) Foreign Application Priority Data
Jul. 29, 2010 (JP) ................................. 2010-170871

(51) Int. Cl.
 *A01H 4/00* (2006.01)
 *C12N 15/90* (2006.01)
 *C12N 15/82* (2006.01)
(52) U.S. Cl.
 CPC ............ *C12N 15/8205* (2013.01); *A01H 4/008* (2013.01)
(58) Field of Classification Search
 None
 See application file for complete search history.

(56) References Cited

U.S. PATENT DOCUMENTS

| 2007/0136898 A1 | 6/2007 | Ishida |
| 2007/0244006 A1 | 10/2007 | Tormo I Blasco et al. |
| 2010/0068812 A1* | 3/2010 | Ishida et al. ................ 435/430 |
| 2010/0132066 A1 | 5/2010 | Ishida et al. |
| 2011/0030101 A1 | 2/2011 | Ishida et al. |
| 2011/0131685 A1 | 6/2011 | Ishida et al. |
| 2012/0124696 A1 | 5/2012 | Ishida et al. |
| 2013/0125265 A1 | 5/2013 | Ishida et al. |

FOREIGN PATENT DOCUMENTS

| WO | WO 96/54961 A2 | 12/1996 |
| WO | WO 02/12520 A1 | 2/2002 |
| WO | WO 02/12521 A1 | 2/2002 |
| WO | WO 2005/017169 A1 | 2/2005 |
| WO | WO 2007/069301 A1 | 6/2007 |
| WO | WO 2007/069543 A1 | 6/2007 |
| WO | WO 2008/105509 A1 | 9/2008 |
| WO | WO 2009/122962 A1 | 10/2009 |
| WO | WO 2011/013764 A1 | 2/2011 |
| WO | 2011-120479 A | 5/2011 |

OTHER PUBLICATIONS

Hensel et al. (Journal of Plant Physiology 165 (2008) 71-82).*
Bartlett et al., "High-throughout Agrobacterium-mediated barley transformation," Plant Methods, vol. 4, No. 22, Sep. 26, 2006, 12 pages.
Cheng et al., "Genetic Transformation of Wheat Mediated by Agrobacterium tumefaciens," Plant Physiol., vol. 115, 1997, pp. 971-980.
Cheng et al., "Invited Review: Factors Influencing Agrobacterium-Mediated Transformation of Monocotyladonous Species," In Vitro Cell Dev. Biol-Plant, vol. 40, Jan.-Feb. 2004, pp. 31-45.
Chu, "The N6 Medium and Its Applications to Anther Culture of Cereal Crops," The Pitman International Series in Applied Biology, Plant Tissue Culture, Aug. 1978, 7 pages.
Frame et al., "Maize (Zea mays L.)," Methods in Molecular Biology, vol. 343, Agrobacterium Protocols, 2/e, vol. 1, Humana Press, Totowa, New Jersey, 2006, pp. 185-199.
Garfinkel et al., "Agrobacterium tumefaciens mutants affected in crown gall tumorigenesis and octopine catabolism," Journal of Bacteriology, vol. 144, No. 2, 1960, pp. 732-743.
harwood et al., "Barley Transformation Using Agrobacterium-Mediated Techniques," Methods in Molecular Biology, Transgenic Wheat, Barley and Oats, vol. 478, 2009, pp. 137-147.
Hensel et al., "Efficient generation of transgenic barley: The way forward to modulate plant-microbe interactions," Journal of Plant Physiology, vol. 165, 2008, pp. 71-82.
Hiei et al., "Efficient transformation of rice (Oryza sativa L.) mediated by Agrobacterium and sequence analysis of the boundaries of the T-DNA," The Plant Journal, vol. 6, No. 2, 1994, pp. 271-282.
Hiei et al., "Improved frequency of transformation in rice and maize by treatment of immature embryos with centrifugation and heat prior to infection with Agrobacterium tumefaciens," Plant Cell Tiss. Organ. Cult., vol. 87, 2008, (Published online Oct. 12, 2006), pp. 233-243.
Ishida et al., "High efficiency transformation of maize (Zea mays L.) mediated by Agrobacterium tumefaciens," Nature Biotechnology, vol. 14, Jun. 1996, pp. 745-750.
Ishida et al., "Improved Protocol for Transformation of Maize (Zea mays L.) Mediated by Agrobacterium temefaciens," Plant Biotechnology, vol. 20, No. 1, 2003, pp. 57-66.
Jacobsen et al., "Barley (Hordeum vulgare L.)," Methods in Molecular Biology, vol. 343; Agrobacterium Protocols, 2/e, vol. 1, Humana Press, Totowa, New Jersey, 2006, pp. 171-183.

(Continued)

*Primary Examiner* — Anne Kubelik
*Assistant Examiner* — Charles Logsdon
(74) *Attorney, Agent, or Firm* — Birch, Stewart, Kolasch & Birch, LLP

(57) ABSTRACT

An object of the present invention is to provide a method of gene introduction, which can transform a *Hordeum* plant at a higher efficiency compared to that in known *Agrobacterium* methods, and a method of producing a transformed *Hordeum* plant. The method of the invention includes a step of subjecting an immature embryo tissue of a *Hordeum* plant to centrifugation treatment and/or pressurization treatment before the inoculation with *Agrobacterium*, during the coculture step, and/or after the coculture step, and is characterized in that the coculture medium satisfies at least one of a) containing an antiauxin; b) containing a cytokinin; and c) containing a phenoxy auxin in an amount of less than 2 μM and/or a benzoic auxin in an amount of less than 5 μM, or not containing any phenoxy auxin and/or benzoic auxin.

13 Claims, 2 Drawing Sheets

(56) References Cited

OTHER PUBLICATIONS

Ke et al., "Manipulation of discriminatory T-DNA delivery by Agrobacterium into cells of immature embryos of barley and wheat," Euphytica, vol. 126, 2002, pp. 333-343.

Unsmaier et al., "Organic Growth Factor Requirements of Tobacco Tissue Cultures," Physiologia Plantarum, vol. 18, 1965, pp. 100-127.

Matthews et al., "Market gene elimination from transgenic barley, using co-transformation with adjacent 'twin T-DNAs' on a standard Agrobacterium transformation vector," Molecular Breeding, vol. 7, 2001, pp. 195-202.

Murashige et al., "A Revised Medium for Rapid Growth and Bio Assays with Tobacco Tissue Cultures," Physiologie Plantarum, vol. 15, 1952, pp. 473-298.

Murray et al., "Comparison of Agrobacterium-mediated transformation of four barley cultivars using the GFP and GUS reporter genes," Plant Cell Rep., vol. 22, 2004, pp. 397-402.

Negrotto et al., "The use of phosphorrannose-Isomerase as a selectable marker to recover transgenic maize plants (*Zea mays* L.) via Agrobacterium transformation," Plant Cell Reports, vol. 19, 2000, pp. 798-803.

Potrykus, "Gene Transfer to Cereals; An Assessment," Biotechnology, vol. 8, Jun. 1990, pp. 535-542.

Serhantova et al., "Callus induction and regeneration efficiency of spring barley cultivars registerd in the Czech Republic," Plant Soil Environ., vol. 50, No. 10, 2004, pp. 456-462.

Tingay et al., "Agrobacterium tumefaciens-mediated barley transformation," The Plant Journal, vol. 11, No. 6, 1997, pp. 1369-1376.

Trifonova et al., "Agrobacterium-mediated transgene delivery and integration into barley under a range of in vitro culture conditions," Plant Science, vol. 161, 2001, pp. 871-880.

Wan et al., "Generation of Large Numbers of Independently Transformed Fertile Barley Plants," Plant Physiol., vol. 104, 1994, pp. 37-48.

Watson et al., "Plasmid Required for Virulence of Agrobacterium tumefaciens," Journal of Bacteriology, vol. 123, No. 1, Jul. 1975, pp. 255-264.

Zhao et al., "Agrobacterium-mediated sorghum transformation," Plant Molecular Biology, vol. 44, 2000, pp. 789-798.

Zhao et al., "High throughout genetic transformation mediated by Agrobacterium tumefaciens in maize," Molecular Breeding, vol. 8, 2001, pp. 323-333.

Extended European Search Report for European Application No. 11812628.3, dated Jan. 22, 2014.

Murashige et al., "A Revised Medium for Rapid Growth and Bio Assays with Tobacco Tissue Cultures," Physiologia Plantarum, vol. 15, 1962, pp. 473-497.

* cited by examiner

METHOD FOR GENE INTRODUCTION INTO HORDEUM PLANT USING AGROBACTERIUM, AND METHOD FOR PRODUCTION OF TRANSFORMED PLANT OF HORDEUM PLANT

TECHNICAL FIELD

The present invention relates to a method of gene introduction into a *Hordeum* plant via *Agrobacterium*. The present invention also relates to a method of producing a transformed *Hordeum* plant via *Agrobacterium*.

BACKGROUND ART

Physicochemical methods (direct introduction of DNA), such as a polyethylene glycol method, an electroporation method, and a particle gun method, and biological methods (indirect introduction of DNA) utilizing functions of *Agrobacterium* are known as methods for transformation of monocotyledons such as barley, wheat, corn, and rice, which are major cereal crops. The direct introduction, however, frequently causes introduction of a fragmented objective gene or introduction of multiple copies of an objective gene. As a result, a transformant that does not express the objective gene or shows abnormal weak expression (gene silencing) appears at a high frequency. A method using a protoplast needs a prolonged culture period, which tends to cause seed sterility or malformation in the resulting transformant due to variation during the culture.

In contrast, in the gene introduction mediated by *Agrobacterium*, for example, the regulation of expression of gene groups in a Ti plasmid virulence region (vir region) maintains the small number of copies of an objective gene and prevents a gene from being introduced as fragmented segments. The gene introduction mediated by *Agrobacterium* therefore has notable advantages of providing a large number of transformants highly expressing the objective gene and allowing the difference in expression levels of individual transformants to be small, compared to the direct gene introduction.

Gene introduction mediated by *Agrobacterium* is generally used for transformation of dicotyledons. Although it has been believed for a long time that hosts of *Agrobacterium* in nature are limited only to dicotyledons and *Agrobacterium* has no ability to infect monocotyledons (Potrykus 2000: Non-Patent Literature 1), a method of transformation of a monocotyledon by *Agrobacterium* at a high efficiency has been first reported in major cereal crops, rice, as a result of detailed studies such as investigation of tissue materials, improvements in medium compositions, and selection of *Agrobacterium* strains (Hiei et al., 1994: Non-Patent Literature 2). Following on the success in rice, examples of successful transformation mediated by *Agrobacterium* in corn (Ishida et al., 1996: Non-Patent Literature 3), wheat (Cheng et al., 1997: Non-Patent Literature 4), barley (Tingay et al., 1997: Non-Patent Literature 5), and sorghum (Zhao et al., 2000: Non-Patent Literature 6) have been reported. As materials of *Agrobacterium*-mediated transformation in monocotyledonous crops, immature embryos and immature embryos cultured for a short period of time are most appropriate, and in crops such as corn, wheat, and barley, immature embryos are main targets of *Agrobacterium* infection (Cheng et al., 2004: Non-Patent Literature 7).

The first successful example of transformation by *Agrobacterium* in barley is also a method using immature embryos as the material (Tingay et al., 1997: Non-Patent Literature 5). As concretely described below, the methods for transformation of barley that have, been recently reported (Jacobsen et al., 2006: Non-Patent Literature 8; Bartlett et al., 2008: Non-Patent Literature 9; Hensel et al., 2008: Non-Patent Literature 10; and Harwood et al., 2008: Non-Patent Literature 11) are also basically the same as the method by Tingay et al. (1997: Non-Patent Literature 5). Though the method by Tingay et al. (1997: Non-Patent Literature 5) includes wounding an immature embryo with a particle gun prior to inoculation with *Agrobacterium*, the wounding treatment is rarely performed since Trifonova et al. (2001: Non-Patent Literature 12) has shown that the wounding treatment of a barley immature embryo with a particle gun prior to inoculation with *Agrobacterium* does not increase the transformation efficiency.

1. Known Technology Using Immature Embryos for Barley Transformation by *Agrobacterium*

1) Isolation of Immature Embryos and Inoculation with *Agrobacterium*

Immature seeds which having immature embryos inside of them at the diameter of 1.5 to 2.0 mm are harvested from ears of barley and are sterilized with a sodium hypochlorite solution to aseptically pick up the immature embryo. The embryonic axis is removed from the obtained immature embryo, and the immature embryo is placed onto a callus induction medium for barley in such a manner that the scutellum side upward. A callus induction medium commonly contains Murashige & Skoog (MS) inorganic salts (Murashige & Skoog, 1962: Non-Patent Literature 13), 30 g/L of maltose, 1.0 g/L of casein hydrolysate, 350 mg/L of myo-inositol, 690 mg/L, 1.0 mg/L of thiamine hydrochloride, 2.5 mg/L of 3,6-dichloro-2-methoxybenzoic acid (dicamba), 1.25 mg/L of $CuSO_4 5H_2O$ (added only in Bartlett et al., 2008: Non-Patent Literature 9; and Harwood et al., 2008: Non-Patent Literature 11), and 3.5 g/L of Phytagel, at pH 5.8 (Jacobsen et al., 2006: Non-Patent Literature 8; Bartlett et al., 2008: Non-Patent Literature 9; Hensel et al., 2008: Non-Patent Literature 10; and Harwood et al., 2008: Non-Patent Literature 11). *Agrobacterium* suspension culture used as an inoculation source is prepared by shaking-culturing *Agrobacterium* in a liquid medium overnight. *Agrobacterium* is inoculated by dropwise applying the *Agrobacterium* suspension onto the scutellum of an immature embryo (Jacobsen et al., 2006: Non-Patent Literature 8; Bartlett et al., 2008: Non-Patent Literature 9; and Harwood et al., 2008: Non-Patent Literature 11) or by immersing an immature embryo in an *Agrobacterium* suspension and then reducing the pressure with a vacuum pump (Hensel et al., 2008: Non-Patent Literature 10). Though the time for inoculation, i.e., the time from the beginning of contact of the *Agrobacterium* suspension with the immature embryo till the transplantation to a coculture medium, is not specifically described in these reports, it may be about 20 minutes to 2 hours in both methods for inoculation, dropping and immersion under reduced pressure. The inoculation of immature embryos with *Agrobacterium* is performed on the day of isolation of the immature embryos or on the following day after overnight culture.

2) Coculture with *Agrobacterium*

The immature embryos inoculated with *Agrobacterium* by dropping or immersion under reduced pressure are transferred to a medium for coculture. The immature embryos are usually placed onto a medium in such a manner that the scutellum faces downward (Jacobsen et al., 2006: Non-Patent Literature 8; Bartlett et al., 2008: Non-Patent Literature 9; Hensel et al., 2008: Non-Patent Literature 10; and Harwood et al., 2008: Non-Patent Literature 11). Regarding the direction of placing immature embryos onto a medium, Hensel et al.

(2008: Non-Patent Literature 10) reported that the transformation efficiency was 29% in coculture by placing the scutellum to face downward, whereas the transformation efficiency was 4.1%, which is about one-seventh that in above, in coculture by placing the scutellum to face upward.

The solid medium for coculture with *Agrobacterium* contains a plant growth regulator, 2.5 mg/L (11.3 µM) of dicamba (Jacobsen et al., 2006: Non-Patent Literature 8; Bartlett et al., 2008: Non-Patent Literature 9; and Harwood et al., 2008: Non-Patent Literature 11). Dicamba in a concentration of 2.5 mg/L (11.3 µM) has been conventionally used for dedifferentiating the scutellum cells of immature embryos and inducing a callus having a regenerating ability (Wan and Lemaux, 1994: Non-Patent Literature 14). The coculture is performed for 2 to 3 days.

3) Selection and Regeneration of Transformed Cell

After coculture, the immature embryos are placed on the above-mentioned callus induction medium supplemented with an antibiotic (e.g., 160 mg/L of timentin) for eradicating *Agrobacterium* and a selective agent such as 50 mg/L of hygromycin. In addition, as a plant growth regulator for inducing a callus, 2.5 mg/L (11.3 µM) of dicamba is commonly used (Jacobsen et al., 2006: Non-Patent Literature 8; Bartlett et al., 2008: Non-Patent Literature 9; Hensel et al., 2008: Non-Patent Literature 10; and Harwood et al., 2008: Non-Patent Literature 11). The immature embryos are subcultured on the same medium at an interval of about 2 weeks to obtain calli (clumps of transformed cells) showing distinct resistance against the selective agent. After about 4 to 6 weeks, the callus resistant to selective agent is transplanted in a pre-regeneration medium (transition medium) containing a selective agent or a regeneration medium (shoot induction medium) containing a selective agent. The callus cultured on a pre-regeneration medium is then transplanted on a regeneration medium containing a selective agent. Subsequently, the regenerated shoots and plantlets are transplanted in a rooting medium containing a selective agent and not containing any plant growth regulator to obtain transformed barley plant bodys.

4) Transformation Efficiency Per Immature Embryo

Transformation efficiencies per immature embryo have been reported as follows:

The transformation efficiencies of a variety, Golden Promise, are 7% (Tingey et al., 1997: Non-Patent Literature 5), 12% (Matthews et al., 2001: Non-Patent Literature 15), 9.2% (Murray et al., 2004: Non-Patent Literature 16), 36% (Bartlett et al., 2008: Non-Patent Literature 9), and 86.7% (Hensel et al., 2008: Non-Patent Literature 10). The high efficiencies reported in Non-Patent Literatures 9 and 10 are limited to some cases and are not stably achieved. The transformation efficiency of a variety, Tafeno, is 2% (Hensel et al., 2008: Non-Patent Literature 10), and that of a variety, Helium, is 2% (Hensel et al., 2008: Non-Patent Literature 10).

2. Known Technology for Gene Introduction Mediated by *Agrobacterium* into Barley Immature Embryo Ke et al., 2002 (Non-Patent Literature 17) evaluated the introduction efficiency of T-DNA into cells of immature embryos by varying the composition of a medium for coculture and analyzing the expression of a β-glucuronidase (GUS) reporter gene after the coculture with *Agrobacterium*. Immature embryos immediately after isolation were inoculated with *Agrobacterium* for 30 minutes and were cocultured for 3 days on a coculture MS medium containing undiluted (×1) or 1/10 diluted (×0.1) basal inorganic salts. The coculture was performed on a coculture medium containing or not containing plant growth regulator, 0.25 mg/L (1.1 µM) of 2,4-dichlorophenoxyacetic acid (2,4-D) which having auxin property. The concentration of 2,4-D, 0.25 mg/L (1.1 µM), is too low to induce the dedifferentiation, and such a concentration is not usually used for callus induction from the scutellum (Serhantova et al., 2004: Non-Patent Literature 18). After the coculture, GUS activity was histochemically observed using 5-bromo-4-chloro-3-indolyl-β-D-glucuronic acid (X-Gluc). The results of observation demonstrate that the efficiency of gene introduction into scutellum cells was high in a medium test group containing MS inorganic salts in a 1/10 concentration, and that the efficiency was further increased in a medium test group containing the MS inorganic salts in a 1/10 concentration and not containing any plant growth regulator (Ke et al., 2002: Non-Patent Literature 17).

These tests described by Ke et al. (2002: Non-Patent Literature 17), however, merely include the effects of various conditions for coculture on the gene introduction efficiency during the coculture, and do not refer to callus formation from immature embryos, selection of transformed cells, and acquisition of transformants at all. Actually, in Non-Patent Literature 17, it is concluded that "However, some extreme conditions have been used in the experiments in order to investigate the impact of particular elements on T-DNA transfer to IEs. . . . It is also conceivable that prolonged culturing in a medium with one-tenth of normal MS medium salt concentration will have a detrimental effect on the plant materials. Therefore, for stable transformations, a fine balance need to be found that enables sufficient number of T-DNA transfer events to occur in the plant material while sufficient number of recipient plant cells still maintain their regenerability". In Non-Patent Literature 17, in all tests using a medium containing MS inorganic salts in a 1/10 concentration, the incubation time from the isolation of immature embryos to the completion of coculture is at least 72 hours (3 days) with or without pre-culture.

3. Known Technology for Gene Introduction Mediated by *Agrobacterium* into Rice and Corn Immature Embryos Hiei et al., (2006: Non-Patent Literature 19) reported that the efficiency of gene introduction into the scutellum cells of immature embryo increases by subjecting rice and corn immature embryos before the inoculation with *Agrobacterium* to a thermal treatment (Patent Literature 1), a centrifugation treatment (Patent Literature 2), or thermal and centrifugation treatments (Patent Literature 3) and that, as a result, the transformation efficiency increases. They also report that even in varieties that could not be transformed until then, transformants can be obtained by performing such treatment. It is also reported that a pressurization treatment (Patent Literature 4) of immature embryos before the inoculation with *Agrobacterium* enhances the efficiency of gene introduction to scutellum cells as in the centrifugation treatment and that, as a result, the transformation efficiency increases. The thermal, centrifugation, thermal and centrifugation, or pressurization treatments are performed to enhance the efficiency of gene introduction to the scutellum of immature embryo.

CITATION LIST

Patent Literature

Patent Literature 1: WO1998/054961
Patent Literature 2: WO2002/012520

Patent Literature 3: WO2002/012521
Patent Literature 4: WO2005/017169
Patent Literature 5: WO2007/069643

Non-Patent Literature

Non-Patent Literature 1: Potrykus, I., (1990), Gene transfer to cereals: an assessment, Bio/technology, 8: 535-542.
Non-Patent Literature 2: Hiei, Y., Ohta, S., Komari, T. and Kumashiro, T., (1994), Efficient transformation of rice (*Oryza sativa* L.) mediated by *Agrobacterium* and sequence analysis of the boundaries of the T-DNA, The Plant Journal, 6: 271-282.
Non-Patent Literature 3: Ishida, Y., Saito, H., Ohta, S., Hiei, Y., Komari, T. and Kumashiro, T., (1996), High efficiency transformation of maize (*Zea mays* L.) mediated by *Agrobacterium tumefaciens*, Nature Biotechnology, 14: 745-750.
Non-Patent Literature 4: Cheng, M., Fry, J. E., Pang, S., Zhou, H., Hironaka, C. M., Duncan, D. R., Conner, T. W., and Wan, Y., (1997), Genetic transformation of wheat mediated by *Agrobacterium tumefaciens*, Plant Physiol., 115: 971-980.
Non-Patent Literature 5: Tingay, S., McElroy, D., Kalla, R., Fieg, S., Wang, M., Thornton, S., and Brettell, R., (1997), *Agrobacterium tumefaciens*-mediated barley transformation, Plant J., 11: 1369-1376.
Non-Patent Literature 6: Zhao, Z.-Y., Cai, T., Tagliani, L., Miller, M., Wang, N., Peng, H., Rudert, M., Schoeder, S., Hondred, D., Seltzer, J., and Pierce, D., (2000), *Agrobacterium*-mediated sorghum transformation, Plant Mol. Biol., 44: 789-798.
Non-Patent Literature 7: Cheng et al., (2004), Invited review: Factors influencing *Agrobacterium*-mediated transformation of monocotyledonous species, In Vitro Cell. Dev. Biol. Plant, 40: 31-45.
Non-Patent Literature 8: Jacobsen et al., (2006), Barley (*Hordeum vulgare* L.) Methods in Molecular Biology, vol. 343, *Agrobacterium* protocols, volume 1, Edited by Kan Wang, Humana Press Inc., Totowa, N.J., 171-183.
Non-Patent Literature 9: Bartlett, J. G., Alves, S. C., Smedley, M., Snape, J. W., and Harwood, W. A., (2008), High-throughput *Agrobacterium*-mediated barley transformation, Plant Methods, 4: 1-12.
Non-Patent Literature 10: Hensel, G., Valkov, V., Middlefell-Williams, J., and Jochen Kumlehn, J. (Efficient generation of transgenic barley: The way forward to modulate plant-microbe interactions, Journal of Plant Physiology, 165: 71-82.
Non-Patent Literature 11: Harwood, W. A., Bartlett, J. G., Alves, S. C., Perry, M., Smedley, M. A., Leyland, N., and Snape, J. W., (2008), Barley transformation using *Agrobacterium*-mediated techniques, Method in Molecular Biology, Transgenic Wheat, Barley and Oats, vol. 478, Jones, H. D. and Shewry, P. R. (eds.), Human Press Inc., Spring Street, N.Y., 137-147.
Non-Patent Literature 12: Trifonova, A., Madsen, S., and Olesen, A., (2001), *Agrobacterium*-mediated transgene delivery and integration into barley under a range of in vitro culture conditions, Plant Science, 161: 871-880.
Non-Patent Literature 13: Murashige, T., and Skoog, F., (1962), A revised medium for rapid growth and bio assays with tobacco tissue cultures, Physiol Plant, 15: 473-497.
Non-Patent Literature 14: Wan, Y. and Lemaux, P. G., (1994), Generation of large numbers of independently transformed fertile barley plants, Plant Physiology, 104: 37-48.
Non-Patent Literature 15: Matthews, P. R., Wang, M-B., Waterhouse, P. M., Thornton, S., Fieg, S. J., Gubler, F., and Jacobsen, J. V., (2001), Marker gene elimination from transgenic barley, using co-transformation with adjacent 'twin T-DNAs' on a standard *Agrobacterium* transformation vector, Molecular Breeding, 7: 195-202.
Non-Patent Literature 16: Murray, F., Brettell, R., Matthews, P., Bishop, D., and Jacobsen, J., (2004), Comparison of *Agrobacterium*-mediated transformation of four barley cultivars using the GFP and GUS reporter genes, Plant Cell Reports, 22: 397-402.
Non-Patent Literature 17: Ke et al., (2002), Manipulation of discriminatory T-DNA delivery by *Agrobacterium* into cells of immature embryos of barley and wheat, Euphytica, 126: 333-343.
Non-Patent Literature 18: Serhantová, V., Ehrenbergerová, J., and Ohnoutková, L., Callus induction and regeneration efficiency of spring barley cultivars registered in the Czech Republic. (2004) Plant, Soil and Environment 50:456-462
Non-Patent Literature 19: Hiei, Y., Ishida, Y., Kasaoka, K., and Komari, T., (2006), Improved frequency of transformation of rice and maize by treatment of immature embryos with centrifugation and heat prior to infection with *Agrobacterium tumefaciens*, Plant Cell Tissue and Organ Culture, 87: 233-243.
Non-Patent Literature 20: Watson et al., (1975), Plasmid required for virulence of *Agrobacterium tumefaciens*, J. Bacteriol., 123: 255-264.
Non-Patent Literature 21: Linsmaier, E., and Skoog, F., (1965), Organic growth factor requirements of tobacco tissue culture, Physiol. Plant., 18: 100-127.
Non-Patent Literature 22: Chu, C.-C., (1978), The N6 medium and its applications to another culture of cereal crops. In: Proc. Symp. Plant Tissue Culture. Peking: Science Press, pp. 43-50.
Non-Patent Literature 23: Cheng et al., (2004), Invited review: Factors influencing *Agrobacterium*-mediated transformation of monocotyledonous species. In Vitro Cell., Dev. Biol. Plant, 40: 31-45.
Non-Patent Literature 24: Negrotto, D., Jolley, M., Beer, S., Wenck, A. R., and Hansen, G., (2000), The use of phosphomannose-isomerase as a selection marker to recover transgenic maize plants (*Zea mays* L) via *Agrobacterium* transformation, Plant Cell Reports, 19: 798-803.
Non-Patent Literature 25: Zhao, Z.-Y., Gu, W., Cai, T., Tagliani, L., Hondred, D., Bond, D., Schroeder, S., Rudert, M., and Pierce, D., (2001), High throughput genetic transformation mediated by *Agrobacterium tumefaciens* in maize, Mol. Breed., 8: 323-333.
Non-Patent Literature 26: Ishida, Y., Saito, H., Hiei, Y., and Komari, T., (2003), Improved protocol for transformation of maize (*Zea mays* L.) mediated by *Agrobacterium tumefaciens*, Plant Biotechnology, 20: 57-66.
Non-Patent Literature 27: Frame et al., (2006), Maize (*Zea mays* L.) Methods in Molecular Biology, vol. 343, *Agrobacterium* protocols, volume 1, Edited by Kan Wang, Humana Press Inc., Totowa, N.J., 185-199.
Non-Patent Literature 28: Garfinkel, D. J., and Nester, E. W., (1980), *Agrobacterium tumefaciens* mutants affected in crown gall tumorigenesis and octopine catabolism, Journal Bacteriology, 1144: 732-43.

SUMMARY OF INVENTION

Technical Problem

It is an object of the present invention to provide a method of gene introduction into *Hordeum* plant for transformation at a higher efficiency compared to that in known *Agrobacterium* methods, and a method of producing a transformed *Hordeum* plant.

Solution to Problem

The present inventors have diligently studied in order to solve the foregoing problems and, as a result, have found that the gene introduction efficiency is enhanced by coculture in a coculture medium satisfying at least one requirements of a) containing an antiauxin, b) containing a cytokinin, and c) containing a phenoxy auxin in an amount of less than 2 μM and/or a benzoic auxin in an amount of less than 5 μM, or not containing any phenoxy auxin and/or benzoic auxin. The coculture medium, however, suppresses callus induction after the coculture, and no transformed plant was practically yielded. In order to deal with this problem, the inventors have investigated the effects of a centrifugation treatment and/or a pressurization treatment of an immature embryonic tissue of a *Hordeum* plant before the inoculation with *Agrobacterium* and/or during or after the coculture in a coculture medium, in addition to the above-mentioned requirements, and have found that the efficiency of callus formation from the immature embryonic tissue of a *Hordeum* plant can be enhanced even under the above-mentioned conditions that suppress callus formation. As a result, the present invention provides transformation of *Hordeum* plants with a high efficiency. The centrifugation treatment and/or pressurization treatment of an immature embryonic tissue may be performed before the inoculation with *Agrobacterium* or after the coculture step.

The present invention is preferably accomplished by the embodiments described below, but is not limited thereto.

Embodiment 1

A method of gene introduction into an immature embryonic tissue of a *Hordeum* plant, the method comprising the steps of:

(i) coculture step by inoculating the tissue with *Agrobacterium* and coculturing the tissue in the presence of the *Agrobacterium* in a coculture medium satisfying at least one of the following conditions a) to c):

a) containing an antiauxin;
b) containing a cytokinin; and
c) containing a phenoxy auxin in an amount of less than 2 μM and/or a benzoic auxin in an amount of less than 5 μM, or not containing any phenoxy auxin and/or benzoic auxin, and (ii) a step of subjecting the tissue to a centrifugation treatment and/or a pressurization treatment before the inoculation with *Agrobacterium*, during the coculture step, and/or after the coculture step.

Embodiment 2

A method of producing a transformed *Hordeum* plant, the method comprising the steps of:

(i) coculture step by inoculating a barley immature embryonic tissue with *Agrobacterium* and coculturing the tissue in the presence of the *Agrobacterium* in a coculture medium satisfying at least one of the following conditions a) to c):

a) containing an antiauxin;
b) containing a cytokinin; and
c) containing a phenoxy auxin in an amount of less than 2 μM and/or a benzoic auxin in an amount of less than 5 μM, or not containing any phenoxy auxin and/or benzoic auxin;

(ii) a step of subjecting the tissue to a centrifugation treatment and/or a pressurization treatment before the inoculation with *Agrobacterium*, during the coculture step, and/or after the coculture step;

(iii) resting step of culturing the tissue on a resting medium; and (iv) regeneration step by regenerating the tissue on a regeneration medium.

Embodiment 3

The method according to Embodiment 1 or 2, wherein the resting step starts within 6 to 36 hours from the beginning of the coculture step.

Embodiment 4

The method according to Embodiment 3, wherein the resting step starts within 12 to 24 hours from the beginning of the coculture step.

Embodiment 5

The method according to Embodiment 1 or 2, wherein the coculture step finishes and the resting step starts within 6 to 36 hours after the isolation of the immature embryo.

Embodiment 6

The method according to Embodiment 5, wherein the coculture step finishes and the resting step starts within 12 to 24 hours after the isolation of the immature embryo.

Embodiment 7

The method according to any one of Embodiments 1 to 6, further comprising the step of physically and/or chemically damaging one or more portions selected from a radicle, a plumule, and an embryonic axis of the immature embryonic tissue before the inoculation of the immature embryonic tissue with *Agrobacterium*, during the coculture step, and/or after the coculture step.

Embodiment 8

The method according to any one of Embodiments 1 to 7, wherein the immature embryonic tissue is cultured in the coculture in such a manner that the scutellum side faces upward and the embryonic axis side is in contact with the coculture medium.

Embodiment 9

The method according to any one of Embodiments 1 to 8, further comprising at least one of the following treatments for transformation efficiency enhancement:

a) a thermal treatment;
b) addition of silver nitrate to the coculture medium; and
c) inoculation with *Agrobacterium* in the presence of a powder.

Embodiment 10

The method according to any one of Embodiments 1 to 9, further comprising the step of selection with a drug between the resting step (iii) and the regenerating step (iv).

Embodiment 11

The method according to any one of Embodiments 1 to 10, wherein the resting medium in the step (iii) and/or a selection medium in the step of selection with a drug contains a plant growth regulator.

Embodiment 12

The method according to any one of Embodiments 1 to 11, wherein the *Agrobacterium* is a bacterium selected from the group consisting of LBA4404, EHA101, EHA105, AGL0, AGL1, and 58C1.

Embodiment 13

The method according to any one of Embodiments 1 to 12, wherein the *Hordeum* plant is barley (*H. vulgare*).

Advantageous Effects of Invention

The present invention enables a *Hordeum* plant to be transformed at a high efficiency. Accordingly, a transformed plant body can be stably obtained with high reproducibility, resulting in reduced costs for obtaining the plant body.

DESCRIPTION OF EMBODIMENTS

Figure 1:
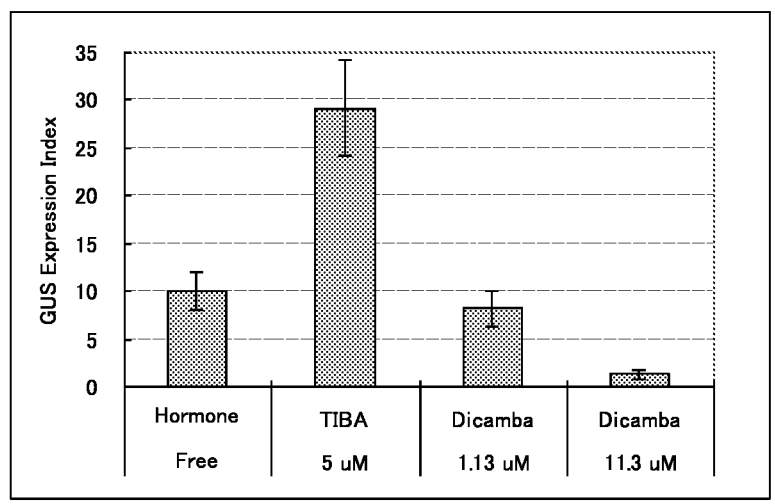
FIG. 1 is a graph showing the effects of addition of antiauxins and dicamba to the coculture medium on the efficiency of gene introduction to barley immature embryos. In each group, 15 immature embryos were used. The columns in FIG. 1 represent the results, from the left, of a system not containing any plant hormones, a system containing an antiauxin: 5 µM TIBA, a system containing a benzoic auxin: 1.13 µM dicamba, and a system of containing 11.3 µM dicamba. The vertical axis in FIG. 1 represents the GUS expression index. The expression of the GUS gene in the scutellum region of each immature embryo was evaluated in seven grades: 87.5 (expressed in 75% or more of scutellum), 62.5 (expressed in 50% or more and less than 75% of scutellum), 37.5 (expressed in 25% or more and less than 50% of scutellum), 17.5 (expressed in 10% or more and less than 25% of scutellum), 6.5 (expressed in 1% or more and less than 10% of scutellum), 0.5 (expressed in exceeding 0% and less than 1% of scutellum), and 0 (no expression), and the average value thereof is shown as the GUS expression index.

The constitution of the present invention will now be specifically described.

The present invention provides a method of gene introduction into an immature embryonic tissue of a *Hordeum* plant, the method comprising the steps of:

(i) coculture step by inoculating the tissue with *Agrobacterium* and coculturing the tissue in the presence of the *Agrobacterium* in a coculture medium satisfying at least one of the following conditions a) to c):

a) containing an antiauxin;
    b) containing a cytokinin; and
    c) containing a phenoxy auxin in an amount of less than 2 µM and/or a benzoic auxin in an amount of less than 5 µM, or not containing any phenoxy auxin and/or benzoic auxin, and (ii) a step of subjecting the tissue to a centrifugation treatment and/or a pressurization treatment before the inoculation with *Agrobacterium*, during the coculture step, and/or after the coculture step.

The present invention further provides a method of producing a transformed *Hordeum* plant, the method comprising the steps of:

(i) coculture step by inoculating a barley immature embryonic tissue with *Agrobacterium* and coculturing the tissue in the presence of the *Agrobacterium* in a coculture medium satisfying at least one of the following a) to c):

a) containing an antiauxin;
    b) containing a cytokinin; and
    c) containing a phenoxy auxin in an amount of less than 2 µM and/or a benzoic auxin in an amount of less than 5 µM, or not containing any phenoxy auxin and/or benzoic auxin;

(ii) a step of subjecting the tissue to a centrifugation treatment and/or a pressurization treatment before the inoculation with *Agrobacterium*, during the coculture step, and/or after the coculture step;

(iii) resting step by culturing the tissue on a resting medium; and (iv) regenerating step by regenerating the tissue on a regeneration medium.

The plant from which the plant tissues can be used in the present invention is that of *Hordeum* plant. Examples of the "*Hordeum*" plant in this specification include, but not limited to, *H. arizonicum, H. bogdanii, H. brachyantherum, H. brevisubulatum, H. bulbosum, H. capense, H. chilense, H. comosum, H. cordobense, H. depressum, H. erectifolium, H. euclaston, H. flexuosum, H. fuegianum, H. guatemalense, H. gussoneanum, H. intercedens, H. jubatum, H. lechleri, H. marinum, H. murinum, H. muticum, H. patagonicum, H. parodii, H. procerum, H. pubiflorum, H. pusillum, H. roshevitzii, H. secalinum, H. stenostachys, H. tetraploidum,* and *H. vulgare*. In the present invention, barley (*H. vulgare*) is particularly preferred. Throughout the specification, the term "barley (*H. vulgare*)" refers to a specific plant species, "barley" belonging to "*Hordeum*".

The plant tissues which can be used in the present invention are immature embryos. Throughout the specification, the teen "immature embryo" refers to an embryo of an immature seed during maturation after pollination. Any stage (maturing stage) of an immature embryo can be used in the method of the present invention without specific limitation, and the immature embryo may be harvested at any stage after pollination, and preferably on 7th to 21st day from pollination. The immature embryo can be used on the day of isolation.

Alternately, a pre-cultured immature embryo may be used. Throughout the specification, the term "mature seed" refers to a fully-ripened seed after completion of maturation after pollination.

Each process mentioned above will be described in detail below.

1. Individual Steps of the Present Invention

The method of gene introduction and the method of production of a transformed plant of the present invention use *Agrobacterium*. These methods can be conducted in accordance with individual steps in known methods of gene introduction and transformation using *Agrobacterium*, unless mentioned otherwise.

(1) The Coculture Step

The present invention involves a coculture step where immature embryos inoculated with *Agrobacterium* are cultured in the presence of the *Agrobacterium*. This step can surely introduce DNA from *Agrobacterium* into plant cells through the culture of the plant tissue inoculated with *Agrobacterium* in the presence of the *Agrobacterium*.

The method of gene introduction or the method of production of a transformed plant of the present invention preferably uses a tissue isolated/harvested from a plant body of a *Hordeum* plant. Accordingly, in the present invention, a tissue (immature embryo) is isolated/harvested from the plant body of a *Hordeum* plant, and then the isolated/harvested tissue is then inoculated with *Agrobacterium*. The isolated/harvested tissue may be pre-cultured, and the cultured tissue may be inoculated with *Agrobacterium*. The tissue is preferably inoculated with *Agrobacterium* on the day of the harvest or on the following day of the harvest. The period of time of the pre-culture of the tissue will be separately described.

The barley immature embryo used in the present invention can have any size and preferably ranges from 1.5 to 2.5 mm.

The above-described immature embryo may be subjected to a thermal treatment for enhancing transformation efficiency (Patent Literature 1). The thermal treatment is performed before the inoculation with *Agrobacterium*. The thermal treatment for enhancing transformation efficiency will be described in detail below.

In the present invention, a tissue of a *Hordeum* plant is inoculated with *Agrobacterium*.

Throughout the specification, the term "inoculation" refers to bringing *Agrobacterium* into contact with a tissue (e.g., the scutellum) of a plant, and various methods for inoculation with *Agrobacterium* are known in the art. Examples of the method include a method involving addition of a plant tissue to a suspension of *Agrobacterium* in a liquid medium, a method involving direct dropwise addition of a suspension of *Agrobacterium* onto a plant tissue on a coculture medium, a method involving injection of a suspension of *Agrobacterium* into a plant tissue, and a method involving immersion of a plant tissue in a suspension of *Agrobacterium* with a reduction of the pressure. In the present invention, however, the method of inoculation with *Agrobacterium* is not limited to these methods.

In the inoculation with *Agrobacterium*, in order to enhance the transformation efficiency by *Agrobacterium*, for example, various additives such as acetosyringone, a surfactant, or a porous ceramic may be added to the suspension of *Agrobacterium*.

Any known *Agrobacterium* can be used in transformation by *Agrobacterium* without limitation in the present invention. In a preferred embodiment of the present invention, the *Agrobacterium* is, for example, LBA4404, EHA101, EHA105, AGL0, AGL1, or C58C1, but is not limited thereto. In the case where a super-binary vector (Non-Patent Literatures 2 and 3) is not used, a bacterial strain containing the virulence region of Ti plasmid pTiBo542 possessed by *Agrobacterium* A281 (Non-Patent Literature 20) is preferably used from the viewpoint of transformation efficiency.

*Agrobacterium* is known to have a property of introducing a gene inserted in T-DNA of a plasmid of the *Agrobacterium* into the genome of a plant. Thus, the *Agrobacterium* that can be used in the present invention has a plasmid where a gene to be expressed in a plant is inserted into T-DNA. A plant can be transformed through inoculation of a tissue of the plant with *Agrobacterium* having this plasmid. A desired characteristic can thereby be provided to the plant cells in the tissue. Examples of the plasmid for *Agrobacterium* that can be used in the present invention include, but not limited to, pSB131, pSB134, pNB131, and pIG121Hm.

The medium used in this step is referred to as "coculture medium" throughout the specification. The coculture medium may be any medium that is usually used for culturing plant cells, and examples thereof include medium based on LS inorganic salts (Non-Patent Literature 21) or N6 inorganic salts (Non-Patent Literature 22). The present invention preferably uses, but not limited to, a medium containing inorganic salts in lower concentrations than those in common medium (e.g., undiluted MS medium). For example, the concentrations of MS inorganic salts contained are reduced to a half or less, more preferably to one-fifth or less, most preferably to one-tenth or less. For example, an MS medium (Non-Patent Literature 17) diluted to a concentration of one-tenth can be most suitably used.

The inventors have diligently studied and have found that the gene introduction efficiency is notably enhanced, as shown in Examples 1 and 2 below, by adding an antiauxin and/or a cytokinin to the coculture medium, by reducing the amount of a phenoxy auxin and/or a benzoic auxin in the coculture medium, by not adding any phenoxy auxin and/or benzoic auxin to the coculture medium, or by combining these conditions. This is one of the most distinctive features of the present invention.

The antiauxin is a material having an effect of antagonistically inhibiting the effect of a compound having an auxin property. In the present invention, the coculture medium can preferably contain the antiauxin such as, but not limited to, 2,3,5-triiodobenzoic acid (TIBA), paclobutrazol, 2,4,6-trichlorophenoxyacetic acid (2,4,6-T), p-chlorophenoxy-isobutyric acid (PCIB), maleic hydrazide, or Uniconazole P.

In the present invention, the coculture medium can preferably contain a cytokinin such as, but not limited to, 6-benzylaminopurine (6BA), kinetin, N-phenyl-N'-(4-pyridylurea) (4-PU), zeatin, thidiazuron, or γ-dimethylallyl aminopterin (2-ip). The concentrations of the antiauxin and the cytokinin contained in the coculture medium are each preferably 0.1 to 20 μM, more preferably 0.5 to 10 μM, and most preferably 2 to 7 μM.

It is generally believed that addition of a phenoxy auxin and/or a benzoic auxin to the coculture medium and the resting medium is important for enhancing dedifferentiation of scutellum cells during the coculture and for easily forming a callus after resting in the resting medium. Accordingly, in the successful examples of reproducible transformation of barley (Tingay et al., 1997: Non-Patent Literature 5; Jacobsen et al., 2006: Non-Patent Literature 8; Bartlett et al., 2008: Non-Patent Literature 9; Hensel et al., 2008: Non-Patent Literature 10; and Harwood et al., 2008: Non-Patent Literature 11), undiluted MS medium containing an auxin in an amount of 10 μM or more have been used. Ke et al. (2002) (Non- Patent Literature 17), however, discloses that a high gene introduction efficiency can be achieved using a 1/10 diluted MS medium not containing any auxin as the coculture medium for barley. Non-Patent Literature 17, however, does not show that a transformed plant is actually produced. In addition, Non-Patent Literature 17 shows that the gene introduction efficiency when an undiluted MS medium not containing any auxin is used is lower than that when the medium contains 2,4-D in a low concentration. Such disclosures in Non-Patent Literature 17 suggest that no addition of the auxin is disadvantageous in light of gene introduction efficiency and that a small amount of 2,4-D is necessary.

The inventors, as shown in Example 1 below, have found that the gene introduction efficiency is enhanced by a lower concentration of a phenoxy auxin and/or a benzoic auxin showing a strong effect of inducing callus formation from the scutellum in the coculture medium. Specifically, the concentration of the phenoxy auxin contained in the coculture medium is, but not limited to, 2 μM or less, preferably 1 μM or less, more preferably 0.5 μM or less, more preferably 0.3 μM or less, and most preferably zero. The concentration of the benzoic auxin contained in the coculture medium is, but not limited to, 5 μM or less, preferably 4 μM or less, more preferably 3 μM or less, more preferably 2 μM or less, and most preferably zero. Furthermore, the coculture medium may contain both the phenoxy auxin and benzoic auxin in these concentrations.

Examples of the phenoxy auxin suitably used in the present invention include, but not limited to, 2,4-dichlorophenoxyacetic acid (2,4-D) and 2,4,5-trichlorophenoxyacetic acid (2,4,5-T). Examples of the benzoic auxin suitably used in the present invention include, but not limited to, 3,6-dichloro-2-methoxybenzoic acid (dicamba) and 4-amino-3,5,6-trichloro-2-pyridinecarboxylic acid (picloram). The coculture medium may further contain other auxins such as indole-3-acetic acid (IAA) and α-naphthaleneacetic acid (NAA).

Incidentally, it is obvious that dedifferentiation and callus formation from scutellum cells are not accelerated in a coculture medium not containing or containing in a low concentration of the phenoxy auxin and/or the benzoic auxin, but containing a cytokinin and/or an antiauxin. Conversely, such conditions suppress dedifferentiation and callus formation. The inventors have found based on these findings that the conditions of suppressing dedifferentiation and callus formation in the coculture step enhance the efficiency of gene introduction to a barley immature embryo. This is one of the distinctive features of the present invention.

It is, however, supposed that these conditions of suppressing dedifferentiation of scutellum cells applied to the coculture medium suppress the callus formation from the scutellum cells in the resting step or selection after the coculture. Actually, the test of Non-Patent Literature 17 performed under conditions not containing any auxin or containing a significantly low concentration of an auxin does not show any evidence of callus formation from immature embryos, selection of transformed cells, and acquisition of transformants at all.

The inventors have actually carried out experiments for transformation of barley using a 1/10 diluted MS medium not containing any plant growth regulator or containing a significantly low concentration, 0.25 mg/L (1.13 μM), of 2,4-D described in Non-Patent Literature 17 as the coculture medium. Unfortunately, the callus formation from cocultured immature embryos was extremely inhibited even if a sufficient amount of an auxin was added to the medium in the resting and the selection steps. As a result, almost no callus was formed.

Basically, Non-Patent Literature 17 merely includes the effects of various conditions for coculture on the gene introduction efficiency during the coculture, and does not suggest direct application of the conditions used in the experiments to transformation. Actually, in Non-Patent Literature 17, it is concluded that "However, some extreme conditions have been used in the experiments in order to investigate the impact of particular elements on T-DNA transfer to IEs. . . . It is also conceivable that prolonged culturing in a medium with one-tenth of normal MS medium salt concentration will have a detrimental effect on the plant materials. Therefore, for stable transformations, a fine balance need to be found that enables sufficient number of T-DNA transfer events to occur in the plant material while sufficient number of recipient plant cells still maintain their regenerability". That is, as obvious from the description above, though Ke et al. have investigated the effects of concentrations of the MS inorganic salts and 2,4-D on the gene introduction efficiency, their recognition was that the concentrations of these materials must be adjusted so as to enhance the regenerating ability, by reducing the gene introduction efficiency, for actually performing stable transformation.

The inventors have, however, anticipated that a callus can be formed while high gene introduction efficiency being maintained even if conditions for suppressing dedifferentiation of scutellum cells are applied to the coculture medium and have further diligently studied. As a result, the inventors have found that even in the scutellum of barley immature embryos cocultured in a coculture medium not containing any auxin or containing a low concentration of an auxin, the callus induction rate can be considerably enhanced by subjecting the immature embryos to a centrifugation treatment before the inoculation with *Agrobacterium*, during the coculture step, and/or after the coculture step; subjecting the immature embryos to a pressurization treatment before the inoculation with *Agrobacterium*, during the coculture step, and/or after the coculture step; or performing both these treatments. The inventors have further found that a callus can be formed, without disadvantages, from the scutellum in the resting step only by performing these treatments, even if the coculture medium is in conditions that suppress callus formation as described above. Incidentally, though these treatments have performed in an MS medium diluted to a 1/10 concentration, no harmful influence on the plant was observed. These findings are the most distinctive features of the present invention. The conditions and effects of the centrifugation treatment and pressurization treatment will be described in detail below.

The coculture medium may contain various additives for further enhancing the transformation efficiency. Examples of the additives include silver nitrate (Non-Patent Literatures 25 and 26) and cysteine (Non-Patent Literature 23).

The term "culture" in this step refers to placing a plant tissue onto a solidified coculture medium or in a liquid coculture medium and then growing the tissue at an appropriate temperature, light-dark condition, and term. In the present invention, the medium can have any form that can sufficiently supply medium components to a plant tissue. The coculture medium can be solidified with a gelling agent known in the art. A typical example of the gelling agent is agarose. The solidified coculture medium can be suitably used in the present invention.

The culture temperature in this step can be appropriately selected and is preferably 18° C. to 30° C. and more preferably 25° C. The culture in this step is preferably performed in a dark place, although not limited thereto.

The culture period in this step can also be appropriately selected. The coculture period in conventional methods is usually 2 to 3 days. In such coculture period, the inventors encounter a problem in that coculture under conditions suppressing dedifferentiation and callus formation of the present invention for 2 to 3 days inhibits the callus formation from immature embryos after the coculture regardless of a treatment such as a centrifugation or pressurization treatment. The inventors have found through diligent studies that the inhibition of callus formation can be solved by shortening the coculture period and that gene introduction can be sufficiently achieved even if the coculture period is shortened. Thus, the coculture period of the present invention is preferably 6 to 36 hours and more preferably 12 to 24 hours.

The inventors have further studied and have found that pre-culture prior to inoculation with *Agrobacterium* inhibits the callus formation from the cocultured barley immature embryos in culturing under conditions where the phenoxy auxin and/or the benzoic auxin is reduced or removed as in the coculture step. Accordingly, in the present invention, the total time of culture from the isolation of immature embryos to the completion of the coculture is preferably 6 to 36 hours and more preferably 12 to 24 hours under conditions where the phenoxy auxin and/or the benzoic auxin is reduced or removed in both the pre-culture and the coculture.

The coculture process in the present invention facilitates gene introduction to the scutellum side of an immature embryo. In order to bring in the effect, the immature embryo can be preferably cultured by being placed in such a manner that the scutellum side faces upward while the embryonic axis side is in contact with the medium. In conventional methods, immature embryos are usually placed on a medium in such a manner that the scutellum side faces downward and is in contact with the medium, which is very different from the present invention (Jacobsen et al., 2006: Non-Patent Literature 8; Bartlett et al., 2008: Non-Patent Literature 9; Hensel et al., 2008: Non-Patent Literature 10; and Harwood et al., 2008: Non-Patent Literature 11).

(2) Centrifugation Treatment and/or Pressurization Treatment

The inventors have found that the present invention provides a notable effect, i.e., sufficient induction of a callus even in barley immature embryos cocultured under conditions that suppress dedifferentiation and callus formation by subjecting the barley immature embryos to a centrifugation treatment before the inoculation with *Agrobacterium*, during the coculture step, and/or after the coculture step. The centrifugation treatment in such a case may be the same as those described in WO2002/012520 (Patent Literature 2). Specifically, the centrifugation acceleration is usually in the range of about 100 to 250000 G, 500 to 200000 G, preferably 1000 to 150000 G, most preferably 1100 to 110000 G. The time for centrifugation is appropriately selected depending on the centrifugal acceleration and is usually 1 sec or more. The upper limit of the centrifugation time is not limited, and the purpose of the treatment can be usually achieved by centrifugation for about 10 min. In the case of high centrifugal acceleration, the gene introduction efficiency can be significantly enhanced by centrifugation for an extremely short time, for example, 1 sec or less. On the contrary, at low centrifugal acceleration, the centrifugation treatment is preferably carried out for a prolonged time. Incidentally, the optimum conditions for centrifugation treatment can be readily determined through routine experiments. As described above, the centrifugation treatment may be performed either before or after excision of the embryonic axis.

In the present invention, the centrifugation treatment may be performed either before or after the coculture or may be performed for the immature embryos extracted during the coculture. Preferably, the centrifugation treatment is performed before and/or after the coculture. Thus, the centrifugation treatment of a plant material is the most distinctive feature of the present invention. The inventors have found that, as shown in Example 3 below, the centrifugation treatment of barley immature embryos before the inoculation with *Agrobacterium* and/or the centrifugation treatment of cocultured immature embryos in a culture system of a coculture medium not containing any plant growth regulator also shows a notable effect of enhancing the rate of callus induction from the barley immature embryos. The inventors have further found that satisfactory callus formation can be observed also in a culture system of a coculture medium containing an antiauxin by performing the centrifugation treatment, as shown in Example 4 below.

A pressurization treatment of immature embryos before the inoculation with *Agrobacterium* and/or a pressurization treatment of cocultured immature embryos also shows a high rate of callus induction from barley immature embryos, as in the centrifugation treatment. The pressurization treatment can be performed by, for example, the method described in WO2005/017169 (Patent Literature 4). The pressurization treatment is performed in a range of, but not limited to, preferably 1.7 to 10 atm and more preferably 2.4 to 8 atm. The time for the pressurization treatment can be appropriately selected depending on the level of the pressure and is preferably from 0.1 second to 4 hours and more preferably from 1 second to 30 minutes. The pressurization treatment may be performed either before or after excision of the embryonic axis.

In the present invention, the pressurization treatment may be performed either before or after the coculture or may be performed during the coculture. Preferably, the pressurization treatment is performed before and/or after the coculture. Thus, the pressurization treatment of a plant material is also the most distinctive feature of the present invention.

Furthermore, in the present invention, both the centrifugation treatment and the pressurization treatment can be suitably performed.

Throughout the specification, the term "before the inoculation with *Agrobacterium*" refers to a treatment performed before the step of inoculation with *Agrobacterium* before the coculture.

Throughout the specification, the term "during the coculture step" refers to a treatment performed during the coculture.

Throughout the specification, the term "after the coculture step" refers to a treatment performed in the resting step that is performed after the coculturing.

Accordingly, throughout the specification, the term "subjecting the tissue to a centrifugation treatment and/or a pressurization treatment before the inoculation with *Agrobacterium*, during the coculture step, and/or after the coculture step" include:

1) an embodiment in which a centrifugation treatment and/or a pressurization treatment is performed before the inoculation with *Agrobacterium*;

2) an embodiment in which a centrifugation treatment and/or a pressurization treatment is performed during the coculture after the inoculation with *Agrobacterium*;

3) an embodiment in which a centrifugation treatment and/or a pressurization treatment is performed after the coculture step and before the resting step;

4) an embodiment in which a centrifugation treatment and/or a pressurization treatment is performed in the resting step; and 5) an embodiment in which a centrifugation treatment and/or a pressurization treatment is performed in a plurality of steps of any of 1) to 4) mentioned above. All the embodiments are within the scope of the present invention.

(3) Resting Step

The method of producing a transformed plant of the present invention further involves a resting step and a regenerating step after the coculture step to produce a transformed plant.

In the resting step, the plant tissue is cultured in a resting medium after the coculture step. This step removes *Agrobacterium* from the plant cells after the coculture step and also proliferates the plant cells.

The medium used in this step is referred to as "resting medium" throughout the specification. The resting medium may be any medium that is usually used for culturing plant cells, and examples thereof include medium based on LS inorganic salts (Non-Patent Literature 21) or N6 inorganic salts (Non-Patent Literature 22). The resting medium in this step preferably contains an antibiotic. The antibiotic contained in the resting medium differs from that used in the selection step described below and is used for eradicating *Agrobacterium*. Cefotaxime and/or carbenicillin is, but not limited to, preferably used as the antibiotic.

The resting medium used in this step preferably contains a plant growth regulator. The plant growth regulator is preferably a benzoic auxin and/or a phenoxy auxin. Since auxins can generally dedifferentiate plant tissues, almost all plant tissues are partially or completely converted to dedifferentiated tissues (calli) in this step and the subsequent selection step. Throughout the specification, the terms "dedifferentiated tissue" and "callus" refer to a tissue that is obtained by culturing a part (explant) of the differentiated plant tissue in a medium containing a plant growth regulator such as an auxin or a cytokinin and is amorphous and undifferentiated cell aggregation not having the shape of the original plant tissue. Accordingly, all embodiments relating to dedifferentiated tissues, for example, a case of subjecting a dedifferentiated tissue to the resting step and a case of completely or partially dedifferentiating a differentiated plant tissue in the resting step or in the subsequent selection step, are within the scope of the present invention.

The term "culture" in this step refers to placing a plant tissue onto a solidified resting medium or in a liquid resting medium and then growing the tissue at an appropriate temperature, light-dark condition, and period. In the present invention, the medium can have any form that ensures sufficient supply of the medium components to a plant tissue. The resting medium can be solidified with a gelling agent known in the art. A typical example of the gelling agent is agarose. The culture temperature in this step can be appropriately selected and is preferably 20° C. to 35° C. and more preferably 25° C. The culture in this step is preferably performed in a dark place, although not limited thereto. The culture period in this step can be also appropriately selected and is preferably 1 to 20 days and more preferably 10 days.

In the resting step in the specification, selection of transformants may be performed. That is, the selection step described below and the resting step may be simultaneously performed. In such a case, any one of the selection medium described below may be used. Such selection of transformants by adding a selective agent to the resting medium is also included in the resting step in the specification.

(4) Selection Step

The selection step and the regenerating step described below are generally performed in transformation of a plant by *Agrobacterium*. The selection step is not indispensable in the method of producing a transformed plant of the present invention. For example, a desired transformant can be obtained through a transformation-improving treatment as described below in place of the selection step. The following description on the selection step is merely exemplification, and the present invention is not limited to the following description.

In this step, a transformant is selected from the tissue obtained in the above-described steps based on whether a gene is introduced or not. The medium that is used in this step, is referred to as "selection medium" throughout the specification. Examples of a selection medium that can be used include medium based on LS inorganic salts (Non-Patent Literature 21) or N6 inorganic salts (Non-Patent Literature 22).

In a typical method of transformation using *Agrobacterium*, the selection medium contains an auxin. Similarly, the selection medium in a preferred embodiment of the present invention contains a plant growth regulator. Any auxin can be used in this selection step without limitation and preferred is dicamba and/or 2,4-D. Furthermore, the selection medium may contain various optional additives.

The transformed plant can be selected by, for example, culturing the plant subjected to the coculture step and/or the resting step in a selection medium containing an appropriate selective agent and selecting one having resistance to the selective agent. Any selective agent that is usually used in the art can be used in this step. For example, an antibiotic or an herbicide can be used as the selective agent. Examples of the antibiotic include hygromycin, chloramphenicol, G418, kanamycin, and blasticidin S, and examples of the herbicide include phosphinothricin, bialaphos, and glyphosate.

In order to perform the selection step, DNA inserted into T-DNA in *Agrobacterium* must include not only the gene to be expressed in the plant but also, for example, a resistance gene against the selective agent. The resistance gene against the selective agent is known in the art. In this step, for example, if the selection is performed with a selection medium containing hygromycin, a gene to be expressed in a plant and a hygromycin resistance gene must be introduced in the plant.

Alternatively, a transformed plant can be selected on the basis of the sugar requirement of plant cells. With sugars assimilable by plant cells, it is known that the plant cell can assimilate sucrose and glucose but not mannose. If a plant tissue is cultured in a medium containing mannose as a main carbon source, the plant tissue dies or does not grow due to the deficiency or lack of assimilable sugar. Selection based on the sugar requirement utilizes this principle. That is, in order to perform this selection process, DNA inserted into T-DNA in *Agrobacterium* must include not only a gene to be expressed in a plant but also a phosphomannose isomerase (PMI) gene. In this case, plant cells containing an introduced PMI gene acquire an ability to assimilate mannose as a carbon source. As a result, only a plant tissue transformed with *Agrobacterium* as described above can grow on a medium containing mannose as a main carbon source, whereby only the transformed plant tissue can be selected (Non-Patent Literature 24). Such a method is also applicable to other sugars. For example, plant cells containing an introduced xylose isomerase gene can utilize xylose as a carbon source and can be therefore applied to such a method.

Alternatively, a readily detectable gene may be introduced as a screening marker to select a transformed plant on the basis of the expression of this gene. Examples of such a gene serving as a screening marker include a GFP gene. Methods for detecting cells or tissues expressing such a gene are known in the art.

This step may be repeated multiple times with medium having different compositions. For example, repeating the selection step multiple times with an increased concentration of selective agent at every selection step enhances the reliability of selection by the agent and the probability of obtaining a transformed plant body. The selection step is preferably performed at least once and more preferably twice. In the case of multiple selection steps, a transformed tissue can also be efficiently acquired by excising the proliferating portion from the tissue cultured in the medium containing the selective agent and subjecting only the proliferating portion to the subsequent selection step.

The term "culture" in this step refers to placing a plant tissue onto a solidified selection medium or in a liquid selection medium and then growing the tissue at an appropriate temperature, light-dark condition, and term. In the present invention, the medium may have any form that allows the medium components to be sufficiently supplied to a plant tissue. The selection medium can be solidified with, for example, agarose, as described above. The culture temperature in this step can be appropriately selected and is preferably 20° C. to 35° C. and more preferably 25° C. The culture in this step is preferably performed in a dark place, although not limited thereto. The culture period in this step can be also appropriately selected. For example, in the case of repeating the selection step twice, the culture is performed for four weeks in total, that is, two weeks for the primary selection and two weeks for the secondary selection. In the case of multiple selection steps, the culture is performed preferably for three to eight weeks, and more preferably four to six weeks, in total. In the multiple selection steps, the culture time, the culture temperature, and light-dark condition may be varied at every selection step.

(5) Regenerating Step

The tissue cultured in the resting medium is, through optional selection, regenerated in a regeneration medium. The medium used in this step is referred to as "regeneration medium" throughout the specification.

The transformation of barley may use a pre-regeneration medium (transition medium). This medium usually contains an auxin (Jacobsen et al., 2006: Non-Patent Literature 8; Bartlett et al., 2008: Non-Patent Literature 9; and Harwood et al., 2008: Non-Patent Literature 11). The pre-regeneration medium may contain a selective agent. The tissue cultured in the pre-regeneration medium is transferred to a regeneration medium and is further cultured.

The regeneration medium may contain a selective agent. Though the selective agent that can be used in this step is the same as that defined in the selection step, the selective agent used in this step is not necessarily the same as that used in the selection step. In such a case, resistance genes against two or more selective agents must be introduced to the plant from Agrobacterium.

The term "regeneration" in the present invention indicates that a completely or partially dedifferentiated plant tissue acquires the properties of the original plant tissue or plant body again. If an auxin is used in the coculture step, the resting step, and/or the selection step, the plant tissue is completely or partially dedifferentiated. Accordingly, the dedifferentiated tissue is regenerated by subjecting the tissue to this step to obtain an intact transformed plant body.

The term "culture" in this step refers to placing a plant tissue onto a solidified regeneration medium or in a liquid regeneration medium and then growing the tissue at an appropriate temperature, light-dark condition, and period. In the present invention, the medium may have any form that allows the medium components to be sufficiently supplied to a plant. The regeneration medium can be solidified with, for example, agarose as described above. The culture temperature in this step can be appropriately selected and is preferably 20° C. to 35° C. and more preferably 25° C. The culture in this step is preferably performed under a bright condition for 16 to 24 hours per day, but is not limited thereto. The culture period can be also appropriately selected and is preferably 7 to 21 days and more preferably 14 days.

2. Treatments for Transformation Efficiency Enhancement Used in the Present Invention The method of gene introduction and the method of production of a transformed plant of the present invention may include treatment for transformation efficiency enhancement described below, in addition to the above-described centrifugation treatment and pressurization treatment. Throughout the specification, the term "treatments for transformation efficiency enhancement" represents a treatment for achieving an enhancement in transformation efficiency. Examples of the treatments for transformation efficiency enhancement include, but not limited to, those shown below and combinations thereof:

a) Addition of silver nitrate ($AgNO_3$) to the coculture medium (see Zhao et al., 2001: Non-Patent Literature 25; and Ishida et al., 2003: Non-Patent Literature 26);

b) A thermal treatment (see WO1998/054961: Patent Literature 1);

c) Inoculation with *Agrobacterium* in the presence of a powder (see WO2007/069643: Patent Literature 5); and g) Addition of cysteine to the coculture medium (Frame et al., 2006: Non-Patent Literature 27).

In these treatments, the thermal treatment and the addition of a powder enhance the gene introduction efficiency, and the addition of silver nitrate increases the callus induction rate.

The addition of silver nitrate to the coculture medium is described in, for example, Zhao et al., 2001 (Non-Patent Literature 25) and Ishida et al., 2003 (Non-Patent Literature 26). Silver nitrate can be added to the coculture medium in a concentration of, for example, 1 to 50 µM, preferably 1 to 10 µM.

The thermal treatment can be performed by, for example, the method described in WO1998/054961 (Patent Literature 1). For example, before being brought into contact with *Agrobacterium*, a plant material is treated at 33° C. to 60° C., preferably 37° C. to 52° C. for 5 seconds to 24 hours, preferably 1 minute to 24 hours.

The inoculation with *Agrobacterium* in the presence of a powder can be performed by, for example, the method described in WO2007/069643 (Patent Literature 5). Specifically, for example, a plant material is inoculated with *Agrobacterium* using a mixture of an *Agrobacterium* suspension and a powder, or a plant in a mixture of the plant and a powder is inoculated with *Agrobacterium*. The powder is not limited, and examples thereof include porous powders, glass wool, and activated charcoal. Porous ceramics, glass wool, and activated charcoal are preferred, and hydroxyapatite, silica gel, and glass wool are more preferred.

With the treatment involving addition of cysteine to a coculture medium, cysteine may be added to the coculturing medium in a concentration of 10 mg/L to 1 g/L, preferably 50 to 750 mg/L, and more preferably 100 to 500 mg/L.

Those skilled in the art can perform these treatments at appropriate timing and conditions. Any combination of these treatments is preferred to further enhance the transformation efficiency. Accordingly, preferred transformation-improving treatments are the addition of $AgNO_3$ to the coculture medium, the thermal treatment, the inoculation with *Agrobacterium* in the presence of a powder, the addition of cysteine to the coculture medium, and combinations thereof. As shown in Examples below, a combination of the thermal treatment and the addition of $AgNO_3$ to the coculture medium is a preferred embodiment of the present invention.

3. Treatment for Physically and/or Chemically Damaging One or More Portions Selected from Radicle, Plumule, and Embryonic Axis The present invention can perform a treatment for physically and/or chemically damaging one or more portions selected from the radicle, plumule, and embryonic axis of an immature embryo tissue before the inoculation with *Agrobacterium*, during the coculture step, and/or after the coculture step.

In the present invention, nonlimiting examples of the method for "physically and/or chemically damaging one or more portions selected from a radicle, a plumule, and an embryonic axis" include various physical and chemical treatments. Examples of the physical treatment include, but not limited to, excision or wounding with an edged knife (for example, a scalpel) and excision or wounding with a tool (for example, tweezers) having a sharp tip. Examples of the chemical treatment include, but not limited to, treatment with an acidic or alkaline substance that causes a loss or reduction in function of plant cells or with an agent such as an herbicide component having cytotoxicity. In the present invention, physical "excision" of one or more portions selected from a radicle, a plumule, and an embryonic axis is a preferred embodiment.

The embryo is a portion that will become a plant body and includes a radicle, a plumule, and an embryonic axis. The embryonic axis is a cylindrical portion that will become the axis of an embryo, and the plumule and the radicle occur from the upper end and the lower end, respectively, of the embryonic axis. Throughout the specification, the radicle, plumule, and embryonic axis should have the same meanings as those usually used in the art.

Throughout the specification, the term "one or more portions selected from a radicle, a plumule, and an embryonic axis" (hereinafter, referred to as "the above-mentioned portion") refers to all the combinations of one, two, or three portions selected from the radicle, the plumule, and the embryonic axis. Specific combinations are: 1) radicle, 2) plumule, 3) embryonic axis, 4) radicle and plumule, 5) radicle and embryonic axis, 6) plumule and embryonic axis, and 7) radicle, plumule, and embryonic axis.

Gene introduction mediated by *Agrobacterium* needs callus formation by dedifferentiation of the plant tissue; hence the existence of the radicle, the plumule, and the embryonic axis inhibits favorable callus formation from a scutellum cell. Accordingly, the excision of the radicle and plumule together with the embryonic axis is a preferred embodiment of the present invention. However, the object of the present invention can be achieved excising only the embryonic axis in the state where the radicle and the plumule have not sprouted yet.

Throughout the specification, the term "before the inoculation with *Agrobacterium*" refers to a treatment performed before the step of inoculation with *Agrobacterium* before coculture.

Throughout the specification, the term "during the coculture step" refers to a treatment performed during the coculture.

Throughout the specification, the term "after the coculture step" refers to a treatment performed in the resting step, which is performed after the coculture step.

Throughout the specification, the term "the step of physically and/or chemically damaging one or more portions selected from the radicle, plumule, and embryonic axis of an immature embryonic tissue before the inoculation of the immature embryonic tissue with *Agrobacterium*, during the coculture step, and/or after the coculture step" includes:

1) an embodiment in which damaging the above-mentioned portion is performed before the inoculation with *Agrobacterium*;

2) an embodiment in which damaging the above-mentioned portion is performed after the inoculation with *Agrobacterium*;

3) an embodiment in which damaging the above-mentioned portion is performed after the coculture step and before the resting step;

4) an embodiment in which damaging the above-mentioned portion is performed in the resting step; and 5) an embodiment in which damaging the above-mentioned portion is performed in a plurality of steps of any of 1) to 4) mentioned above. All the embodiments are within the scope of the present invention.

4. Advantageous Effect by the Method of the Present Invention

A *Hordeum* plant can be transformed at a stable and high efficiency through the method of gene introduction of the present invention and the method of production of a transformed plant of the present invention. Accordingly, the transformation efficiency of a plant can be enhanced.

Throughout the specification, the term "high transformation efficiency" represents a comprehensive concept including high-efficiency introduction of a target gene into a plant cell, high-efficiency induction of a callus from, for example, an immature embryo, and high-efficiency regeneration occurring from the transformed callus. Throughout the specification, the term "enhanced transformation efficiency" is a comprehensive concept including the enhanced introduction efficiency of a target gene into a plant cell, an increased callus induction rate from, for example, an immature embryo, and the enhanced regeneration efficiency from a transformed callus.

The introduction of a gene into a plant tissue can be confirmed by various known processes. For example, the transformation can be confirmed by using a gene that is transformed as a reporter gene such as a β-glucuronidase (GUS) gene, a luciferase gene, or a GFP gene and visually observing the expression site of the reporter gene by a simple known method. Alternatively, the transformation can be confirmed by using a selection marker gene such as an antibiotic resistance gene or an herbicide resistance gene, and observing the expression of the resistance as an indicator by culturing the plant cells in a medium containing an antibiotic or an herbicide or treating the plant with a solution of an antibiotic or an herbicide.

EXAMPLES

The present invention will now be described with reference to examples below, which are not intended to limit the technical scope of the invention. The scope of the present invention is defined by the appended claims. Based on description in the specification, modifications and changes will be apparent to those skilled in the art.

Example 1

Effect of Coculture Medium Composition on Gene Introduction Efficiency (Antiauxin, Auxin)

Material and Method

Immature embryos (size: 1.5 to 2.0 mm) of barley (variety: Golden Promise) from which embryonic axes were removed were aseptically collected and were immersed in 1 mL of sterilized water in a 2-mL microtube. In order to enhance the gene introduction efficiency, the tube containing the immature embryos was heated in a water bath at 43° C. for 5 minutes. An *Agrobacterium* strain EHA101 having a hygromycin resistance gene (pIG121Hm) (Non-Patent Literature 2) was suspended in an MG/L liquid medium (Non-Patent Literature 28) containing 100 µM acetosyringone and was shake-cultured (180 rpm) at 28° C. overnight (about 20 hours) to prepare an inoculation source. The bacterial concentration was adjusted to an O.D. of 1.0 (660 nm). The inoculation source was added to the thermal-treated immature embryos, and a reduced pressure treatment was performed with a vacuum pump at 500 mbar for 10 minutes. The immature embryos were washed once with a callus induction liquid medium, CIMT (Tingay et al., 1997: Non-Patent Literature 5) not containing any plant growth regulator (hereinafter, antiauxins, cytokinins, and auxins are collectively referred to as plant growth regulators). The immature embryos inoculated with *Agrobacterium* were transplanted onto a barley coculture medium (1/10 diluted MS inorganic salts and MS vitamins, 10 g/L of glucose, 0.5 g/L of MES, 5 µM $AgNO_3$, and 5 µM $CuSO_4$, pH 5.8; and 8 g/L of agarose) containing 100 µM acetosyringone in such a manner that the scutellum side faces upward. The test was performed using two plant growth regulators in four test groups of the coculture medium. That is, the four test groups are a hormone-free test group not containing any plant growth regulator, a test group of 5 µM TIBA (antiauxin), a test group of 1.13 µM dicamba (auxin), and a test group of 11.3 µM dicamba (auxin).

Immature embryos cultured at 25° C. in the dark for 24 hours were transplanted in a CIMT resting medium (Tingay et al., 1997: Non-Patent Literature 5) containing 0.5 mg/L of 2,4-D and 1.25 mg/L of $CuSO_4.5H_2O$. The resting medium was added with 250 mg/L of carbenicillin and 100 mg/T, of cefotaxime for *Agrobacterium* eradication. The immature embryos were cultured at 25° C. in the dark for 2 days cultured and were then immersed in a 0.1 M phosphate buffer solution (pH 6.8) containing 0.1% Triton X-100 and were left in the solution at 37° C. for 1 hour. The phosphate buffer solution was removed, and a phosphate buffer solution containing 1.0 mM 5-bromo-4-chloro-3-indolyl-β-D-glucuronic acid (X-gluc) and 20% methanol was added thereto. After treatment at 37° C. overnight, the expression of a GUS gene was investigated. The expression of the GUS gene in the scutellum region of each immature embryo was evaluated in seven grades: 87.5 (expressed in 75% or more of scutellum), 62.5 (expressed in 50% or more and less than 75% of scutellum), 37.5 (expressed in 25% or more and less than 50% of scutellum), 17.5 (expressed in 10% or more and less than 25% of scutellum), 6.5 (expressed in 1% or more and less than 10% of scutellum), 0.5 (expressed in exceeding 0% and less than 1% of scutellum), and 0 (no expression), and the average value thereof was expressed by a numerical value as the GUS expression index. Each group used 15 immature embryos for the test.

Results and Discussion

The gene introduction efficiency was the lowest in the test group of 11.3 µM dicamba (Tingay et al., 1997: Non-Patent Literature 5; Jacobsen et al., 2006: Non-Patent Literature 8; Bartlett et al., 2008: Non-Patent Literature 9; Hensel et al., 2008: Non-Patent Literature 10, and Harwood et al., 2008: Non-Patent Literature 11), which is most widely used in transformation of barley by *Agrobacterium* using the immature embryo (FIG. 1, the fourth column). The gene introduction efficiency by addition of 1.13 µM dicamba (FIG. 1, the third column) was a similar level to that of the plant growth regulator-free test group (FIG. 1, the first column). This is similar to the result obtained by Ke et al. (2002: Non-Patent Literature 17) using a 1/10 diluted MS coculture medium containing 2,4-D. The addition of an antiauxin (5 µM TIBA) notably enhanced the efficiency of gene introduction to the scutellum of barley immature embryo (FIG. 1, the second column).

Example 2

Effect of Coculture Medium Composition on Gene Introduction Efficiency (Cytokinin, Antiauxin)

Material and Method

The materials and the method of inoculation with *Agrobacterium* were the same as those in Example 1. The coculture medium used consisted of six test groups containing different five plant growth regulators: a hormone-free test group not containing any plant growth regulator; three test groups of cytokinins: 5 µM 6BA, 5 µM 4-PU, and 5 µM zeatin; and two test groups of antiauxins: 5 µM TIBA and 5 µM paclobutrazol. Immature embryos cultured at 25° C. in the dark for 24 hours were transplanted in a CIMT resting medium (Tingay et al., 1997: Non-Patent Literature 5) containing 0.5 mg/L of 2,4-D and 1.25 mg/L of $CuSO_4.5H_2O$, as in Example 1, and further containing 250 mg/L of carbenicillin and 100 mg/L of cefotaxime for *Agrobacterium* eradication. The immature embryos were cultured at 25° C. in the dark for 2 days and were then investigated for the expression of a GUS gene as in Example 1. The results were expressed by a numerical value as the GUS expression index. Each group used 15 immature embryos for the test.

Results and Discussion

Figure 2:
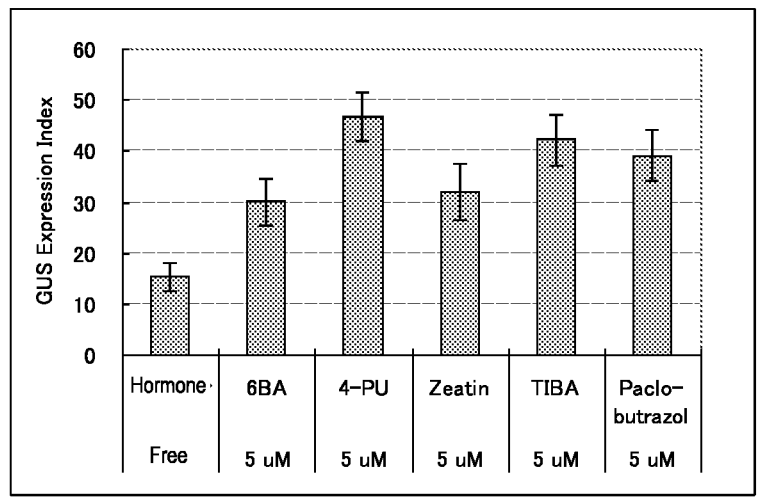
FIG. 2 is a graph showing the effects of addition of cytokinins and antiauxins to the coculture medium on the efficiency of gene introduction to barley immature embryos. In each group, 15 immature embryos were used. The columns in FIG. 2 represent a system not containing any plant hormone, a system containing 5 µM 6BA, a system containing 5 µM 4-PU, a system containing 5 µM zeatin, a system of 5 µM TIBA, and a system of 5 µM paclobutrazol. 6BA, 4-PU, and zeatin are cytokinins. TIBA and paclobutrazol are antiauxins. The vertical axis in FIG. 2 represents the GUS expression index. The GUS expression index in FIG. 2 was determined as in FIG. 1.

The gene introduction efficiency of the group not containing any plant growth regulator was the lowest, as shown by an index of about 15 (FIG. 2, the first column). Other groups containing cytokinins or antiauxins showed an index of 30 or more (FIG. 2, the second to the sixth columns). This first revealed that the efficiency of gene introduction to the scutellum of barley immature embryo is notably enhanced by addition of a cytokinin or an antiauxin to the coculture medium.

Example 3

Effect of Centrifugation Treatment on Compact Callus Formation

Material and Method

The materials and the method of inoculation with *Agrobacterium* were the same as those in Example 1. The coculture medium did not contain any plant growth regulator. Immature embryos cocultured at 25° C. in the dark for 24 hours were transferred in a 2-mL microtube containing 1 mL of sterilized water and were centrifuged at 25° C. at 1500 rpm (20000×g) for 10 minutes. Subsequently, the immature embryos were transplanted in a CIMT resting medium (Tingay et al., 1997: Non-Patent Literature 5) containing 0.5 mg/L of 2,4-D and 1.25 mg/L of $CuSO_4.5H_2O$, as in Example 1. Meanwhile, the resting medium contained 250 mg/L of carbenicillin and 100 mg/L of cefotaxime for *Agrobacterium* eradication. The immature embryos were cultured at 25° C. in the dark for 2 days, and then the scutellum of each immature embryo was divided into four sections. The divided sections were transplanted in a medium having the same composition and were further cultured under the same culture conditions for 8 days. After the culture, the shape of the callus formed on the scutellum section was observed. In barley, only the compact callus having an embryogenic shape can be subcultured and has a regenerating ability, whereas a sponge-like callus containing a large amount of moisture is often formed. Such a callus does not have the regenerating ability anymore. Accordingly, the scutellum sections that formed a compact callus were counted to provide a callus-forming rate.

Results and Discussion

The test group subjected to the centrifugation treatment formed compact calli at an efficiency of 80% (Table 1, the lower column), whereas the test group not subjected to the centrifugation treatment formed compact calli in only about a quarter thereof, 17.5% (Table 1, the upper column). Ke et al. (2002: Non-Patent Literature 17) showed that the gene introduction efficiency in a coculture medium not containing any plant growth regulator is enhanced to a certain extent. This literature states that "prolonged culturing in a medium with one-tenth of normal MS medium salt concentration will have a detrimental effect on the plant materials" and that "for stable transformation, a fine balance need to be found that enables sufficient number of T-DNA transfer events to occur in the plant material while sufficient number of recipient plant cells still maintain their regenerability". In fact, the compact callus formation from a scutellum cell as a gene introduction region is strongly suppressed when the resting culture is performed without any treatment. In contrast, in the test group subjected to the centrifugation treatment, 80% of immature embryos formed compact calli; the results suggest that a transformed callus could be obtained at a certain frequency by the subsequent selection with hygromycin. The inventors have found that a centrifugation treatment or a pressurization treatment of immature embryos before the inoculation with *Agrobacterium* also similarly accelerates callus formation. Furthermore, in this experimental system, the centrifugation treatment and the pressurization treatment of immature embryos before the inoculation with *Agrobacterium* did not enhance the efficiency of gene introduction to the cocultured immature embryos and accelerated absolutely only compact callus formation.

TABLE 1

Callus formation after resting depending on centrifugal treatment after coculture

| Centrifugal treatment after coculture | Number of immature embryos tested | Number of scutellum sections tested (a) | Number of scutellum sections formed compact callus (b) | Efficiency (b/a: %) |
|---|---|---|---|---|
| − | 10 | 40 | 7 | 17.5 |
| + | 10 | 40 | 32 | 80.0 |

Example 4

Effect of Centrifugation Treatment on Formation of Hygromycin Resistance Callus

Material and Method

The materials, the method of inoculation with *Agrobacterium*, the thermal treatment conditions, the coculture step, the centrifugation treatment conditions, and the resting step were the same as those in Example 3. The coculture medium contained an antiauxin: 5 μM TIBA. The scutellum was divided into four sections, and the resting step was further continued for 10 days. After the resting step, each divided scutellum section was further divided into 4 subsections (i.e., one immature embryo was divided into 16 sections). The divided subsections were transplanted in a CIMT selection medium (Tingay et al., 1997: Non-Patent Literature 5) containing 50 mg/L of hygromycin B and 1.25 mg/L of $CuSO_4.5H_2O$. The selection medium was added with 250 mg/L of carbenicillin for *Agrobacterium* eradication. Scutellum subsections were sorted by the original immature embryo and placed on the medium. After the culture at 25° C. in the dark for 2 weeks, only compact calli were selected by removing sponge-like calli containing a large amount of moisture. The compact calli were transplanted in a secondary selection medium having the same composition and were cultured for further 3 weeks under the same conditions. After the culture, hygromycin resistance compact calli propagated on the selection medium were counted. Note that even when a plurality of resistance calli were formed from scutellum subsections derived from a single immature embryo, only one of the resistance calli was counted as a hygromycin resistance callus for each immature embryo.

In order to compare the present invention with a conventional method of transformation, transformation in accordance with the protocol described in Harwood et al. (2008: Non-Patent Literature 11) was performed. Unlike the above-described Examples, an undiluted (×1) MS medium containing 2.5 mg/L of dicamba was used as the coculture medium. The resting medium not containing 2,4-D was used in accordance with the protocol in Harwood et al. (2008), which was also different from the above-described Examples. Meanwhile, in order to adjust the conditions to the same as those in Examples, a thermal treatment was performed under the same conditions as those for other test groups for enhancing gene introduction, and also the inoculation with *Agrobacterium* was performed under reduced pressure as in other test groups. The composition of the selection medium was the same as that in the other test groups.

Results and Discussion

In the conventional method in accordance with a modified protocol of Harwood et al. (2008: Non-Patent Literature 11), the gene introduction efficiency (GUS expression) on the second day after the completion of the coculture was low, compared with those in the test group not subjected to the centrifugation treatment and the test group subjected to the centrifugation treatment (data not shown). Compact calli were, however, formed in the resting step without any problem. The number of calli survived in the selection with hygromycin was small compared with that in the centrifugation treatment test group, and the eventual efficiency after the secondary selection was only 33.3% (Table 2, the upper column). Though the gene introduction efficiency of the immature embryos not subjected to the centrifugation treatment after the coculture was high, almost no compact callus was formed, and no callus survived in the selection medium (Table 2, the middle column). In the transformation system involving the centrifugation treatment after the coculture, a large number of compact call were formed, and the hygromycin resistance callus was formed from 80% of immature embryos after the secondary selection (Table 2, the lower column). The results demonstrate that the scutellum cell of an immature embryo showing a high gene introduction efficiency by the effect of an antiauxin TIBA, does not achieve usual callus formation when a centrifugation treatment is not performed, but the centrifugation treatment allows a compact callus to be formed mostly like the usual callus formation and also allows the callus to be selected in the selection step as in the conventional method.

TABLE 2

Efficiency of hygromycin-resistant callus formation depending on centrifugal treatment after coculture

| Test group | Number of immature embryos Inoculation (a) | Hygromycin-resistant callus formation (b) | Frequency of hygromycin-resistant callus formation (b/a: %) |
|---|---|---|---|
| Conventional method* | 15 | 5 | 33.3 |
| Without centrifugal treatment | 15 | 0 | 0.0 |
| With centrifugal treatment | 15 | 12 | 80.0 |

Example 5

Effect of Coculture Medium Composition on Gene Introduction Efficiency (Hormone-Free, 2,4-D)

Material and Method

The materials and the method of inoculation with *Agrobacterium* were the same as those in Example 1. That is, a culture medium containing 1/10 diluted MS inorganic salts was used. The test groups used consisted of the following three types: a hormone-free coculture medium not containing any plant growth regulator, a coculture medium containing 1.13 µM 2,4-D, and a coculture medium containing 11.3 µM 2,4-D. Immature embryos cocultured at 25° C. in the dark for 24 hours were transplanted in a CIMT resting medium (Tingay et al., 1997: Non-Patent Literature 5) containing 0.5 mg/L of 2,4-D and 1.25 mg/L of $CuSO_4 \cdot 5H_2O$ as in Example 1. The resting medium was added with 250 mg/L of carbenicillin and 100 mg/L of cefotaxime for *Agrobacterium* eradication. The immature embryos were cultured at 25° C. in the dark for 2 days and were then investigated for expression of a GUS gene as in Example 1. The results were expressed by a numerical value as the GUS expression index. Each group used 15 immature embryos for the test.

Results and Discussion

Figure 3:
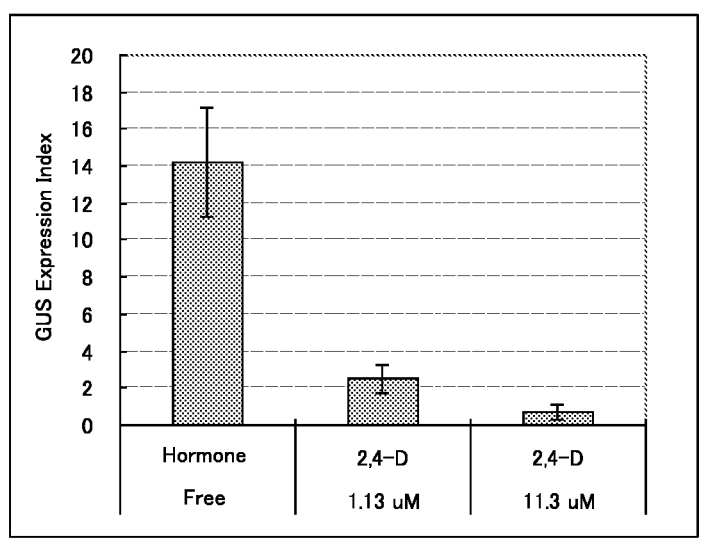
FIG. 3 is a graph showing the effects of addition of 2,4-D to the coculture medium on the efficiency of gene introduction to barley immature embryos. In each group, 15 immature embryos were used. The columns in FIG. 3 represent the results, from the left, of a system not containing any plant hormones, a system containing a phenoxy auxin: 1.13 µM 2,4-D, and a system containing 11.3 µM 2,4-D. The vertical axis in FIG. 3 represents the GUS expression index. The GUS expression index in FIG. 3 was determined as in FIG. 1.

The hormone-free coculture medium not containing any plant growth regulator showed the highest gene introduction efficiency (FIG. 3, the first column), whereas the coculture medium containing 11.3 µM 2,4-D showed the lowest gene introduction efficiency (FIG. 3, the third column). The gene introduction efficiency in the coculture medium added with 1.13 µM 2,4-D was also very low, i.e., about one-sixth that of the hormone-free coculture medium (FIG. 3, the second column). This result significantly differs from the result in Example 1 where the gene introduction efficiency in the test group added with 1.13 µM dicamba, which is an auxin like 2,4-D, was equal to that of the hormone-free test group (FIG. 1, the first and the third column). This demonstrates that there are a difference in effect of concentrations of auxins on gene efficiency between a phenoxy auxin, 2,4-D, and a benzoic auxin, dicamba, which probably results from a slight difference in action between the both.

Example 6

Effect of Centrifugation Treatment Before Inoculation with *Agrobacterium* and after Coculture on Compact Callus Formation Material and Method The preparation of materials and the inoculation with *Agrobacterium* were performed as in Example 1. The thermal treatment of immature embryos was also similarly performed. The coculture medium was added with 5 µM TIBA.

Test group (1) performing centrifugation treatment before inoculation with *Agrobacterium*: Isolated immature embryos were transferred in a 2-mL microtube containing 1 mL of sterilized water and were centrifuged at 25° C. at 15000 rpm (20000×g) for 10 minutes, followed by inoculation with *Agrobacterium*.

Test group (2) performing centrifugation after coculture: After the coculture for 24 hours as in Example 4, the immature embryos were transferred in a 2-mL microtube containing 1 mL of sterilized water and were centrifuged at 25° C. at 15000 rpm (20000×g) for 10 minutes. The culturing process and the culture period of the resting culture and subsequent culture were as in Example 4.

Results and Discussion

In the test group subjected to the centrifugation treatment before the inoculation with *Agrobacterium* (test group 1, Table 3, the upper column) and the test group subjected to the centrifugation treatment after the coculture (test group 2, Table 3, the lower column), compact calli were formed at similar high efficiencies from the scutellum cells serving as a gene introduction region. That is, the callus formation was enhanced by the centrifugation treatment before the inoculation with *Agrobacterium* and also by the centrifugation treatment after the coculture. In addition, the callus formation was similarly enhanced by applying a pressure of 7100 hPa for five minutes to immature embryos in sterilized water, and no difference in the effects was observed between the pressurization treatment before the inoculation with *Agrobacterium* and the pressurization treatment after the coculture. After both the centrifugation treatment and the pressurization treatment were performed before the inoculation with *Agrobacterium*, the gene introduction efficiency was not substantially enhanced. Furthermore, tests were performed by prolonging the coculture period to 48 hours (2 days) or 72 hours (3 days) using the same coculture medium as in Example 6. However, the callus formation was strongly suppressed, and almost no compact callus having a regenerating ability was formed from the immature embryo in the resting medium even when the centrifugation treatment with the same strength was performed before the inoculation with *Agrobacterium* or after the coculture.

TABLE 3

Comparison of callus formation efficiencies in centrifugal treatment before inoculation with *Agrobacterium* and centrifugal treatment after coculture

| Test group | The time of centrifugal treatment | Number of immature embryos tested | Number of scutellum sections tested (a) | Number of scutellum sections formed compact callus (b) | Efficiency (b/a: %) |
|---|---|---|---|---|---|
| 1 | before inoculation | 10 | 40 | 34 | 85.0 |
| 2 | after coculture | 10 | 40 | 37 | 92.5 |

Example 7

Comparison of Transformation Efficiency Between Conventional Coculture Medium Containing Dicamba and Coculture Medium Containing 1/10 Diluted MS Inorganic Salts The preparation of materials and the inoculation with *Agrobacterium* were performed as in Example 1. The thermal treatment was also similarly performed.

Test group (1): Immature embryos inoculated with *Agrobacterium* were placed on the coculture medium described in Harwood et al. (2008: Non-Patent Literature 11) in such a manner that the scutellum faces downward. The coculture was performed at 25° C. in the dark for 3 days. In this test group, the centrifugation treatment was not performed.

Test group (2): Isolated immature embryos were transferred in a 2-mL microtube containing 1 mL of sterilized water and were centrifuged at 25° C. at 15000 rpm (20000×g) for 10 minutes. Subsequently, coculture was performed as in test group (1).

Test group (3): Immature embryos cocultured as in test group (1) were transferred in a 2-mL microtube containing 1 mL of sterilized water and were centrifuged at 25° C. at 15000 rpm (20000×g) for 10 minutes.

Test group (4): Immature embryos inoculated with *Agrobacterium* were transferred onto a barley coculture medium (1/10 diluted MS inorganic salts and MS vitamins, 10 g/L of glucose, 5 μM TIBA, 0.5 g/L of MES, 5 μM $AgNO_3$, and 5 μM $CuSO_4$, pH 5.8; and 8 g/L of agarose) containing 100 μM acetosyringone in such a manner that the scutellum side faces upward. The immature embryos were cultured at 25° C. in the dark for 24 hours. In this test group, the centrifugation treatment was not performed.

Test group (5): Isolated immature embryos were transferred in a 2-mL microtube containing 1 mL of sterilized water and were centrifuged at 25° C. at 15000 rpm (20000×g) for 10 minutes. Subsequently, coculture was performed as in test group (4).

Test group (6): Immature embryos cocultured as in test group (4) were transferred in a 2-mL microtube containing 1 mL of sterilized water and were centrifuged at 25° C. at 15000 rpm (20000×g) for 10 minutes.

Test group (7): Immature embryos were cocultured as in test group (4) except that the plant growth regulator, TIBA, was not contained in the coculture medium and were then transferred in a 2-mL microtube containing 1 mL of sterilized water and were centrifuged at 25° C. at 15000 rpm (20000×g) for 10 minutes.

That is, test groups (1), (2), and (3) used a coculture medium containing an auxin, dicamba, and undiluted MS inorganic salts, whereas test groups (4), (5), and (6) used a coculture medium containing an antiauxin, TIBA, and 1/10 diluted MS inorganic salts. Test group (7) used a hormone-free coculture medium containing 1/10 diluted MS inorganic salts.

The immature embryos prepared in test groups (1) to (7) were each transplanted in a CIMT resting medium (Tingay et al., 1997: Non-Patent Literature 5) containing 0.5 mg/L of 2,4-D, but not containing any selective agents. The resting medium was added with 250 mg/L of carbenicillin and 100 mg/L of cefotaxime for *Agrobacterium* eradication. The immature embryos were cultured at 25° C. in the dark for 7 days and were each divided into four sections. The divided sections were transplanted in a CIMT resting medium (Tingay et al., 1997: Non-Patent Literature 5) containing 0.2 mg/L of 2,4-D and 5 μM $CuSO_4$, but not containing any selective agent. After the resting culture at 25° C. in the dark for 10 days, each four-divided immature embryo section was further divided into three to six subsections (i.e., one immature embryo was divided into 12 to 24 sections). The divided subsections were placed on a CIMT selection medium (Tingay et al., 1997: Non-Patent Literature 5) containing 0.1 mg/L of 2,4-D, 1.5 μM $CuSO_4$, and 75 mg/L of hygromycin and were cultured at 25° C. in the dark for 10 days. Subsequently, subsections having cell clump supposed to be hygromycin resistance were subcultured in a selection medium having the same composition and were cultured at 25° C. in the dark for 10 days.

One hygromycin resistance callus for each divided section was placed on a transition (regeneration preculture) medium (Harwood et al. (2008: Non-Patent Literature 11)) not containing hygromycin and was cultured at 25° C. in the dark for about 2 weeks. The resulting greening cell clump or shoot was placed on a regeneration medium (Harwood et al. (2008: Non-Patent Literature 11)) containing 30 mg/L hygromycin, 0.2 mg/L indolebutyric acid (IBA), and 5 μM $CuSO_4$ and was cultured at 25° C. in the light for about 2 weeks.

An excised part of a leaf of the resulting hygromycin-resistant plant body was immersed in a 0.1 M phosphate buffer solution (pH 6.8) containing 0.1% Triton X-100® and was left in the solution at 37° C. for 1 hour. The phosphate buffer solution was removed, and another phosphate buffer solution containing 1.0 mM 5-bromo-4-chloro-3-indolyl-β-D-glucuronic acid (X-gluc) and 20% methanol was added thereto. After treatment at 37° C. for 24 hours, the expression of a GUS gene was investigated. The GUS gene expression was investigated for one leaf from one plant body at most for each divided immature embryo section.

Results and Discussion

In transformation using the conventional coculture medium containing an auxin, dicamba, the transformation efficiency per immature embryo was 30% in test group 1 (without centrifugation treatment) and was 20% in test group 3 (centrifugation treatment after coculture) (Table 4), whereas three test groups performing centrifugation treatment of immature embryos and using the coculture medium containing 1/10 diluted MS inorganic salts showed very high transformation efficiency: 90% in test group 5 (centrifugation treatment before inoculation with *Agrobacterium*), 100% in test group 6 (centrifugation treatment after coculture), and 80% even in test group 7 (hormone-free coculture medium and centrifugation treatment after coculture). In test group 4 not subjecting immature embryos to centrifugation treatment, no compact callus having a regenerating ability was formed, and no transformant was obtained at all. In addition, no transformant was obtained at all from the immature embryos in test group 2 involving the culture in the conventional coculture medium containing dicamba after the centrifugation treatment. This is caused by the introduction of T-DNA into an immature embryo at a portion where no callus is formed later by the centrifugation treatment before the coculture. Actually, a GUS assay after the coculture detected the expression of a GUS gene near the center of an immature embryo at the embryonic axis side. The transformation efficiency in test group 6 using the coculture medium containing an antiauxin, 5 μM TIBA, was higher than that in test group 7 of hormone-free.

As described above, a considerable increase in transformation efficiency was recognized in the test groups using a coculture medium containing an antiauxin, 5 μM TIBA and in a coculture medium not containing any plant growth regulator by performing centrifugation treatment (test groups 5, 6, and 7). The effects were the same between the case of performing the centrifugation treatment before the inoculation with *Agrobacterium* (test group 5) and the case of performing after the coculture (test groups 6 and 7). In contrast, in the test group using a coculture medium containing 11.3 µM dicamba (benzoic auxin), which is conventionally used, an enhancement in transformation efficiency by a centrifugation treatment was not recognized (test groups 2 and 3). The results evidently demonstrate the effects of the present invention that a objective gene is introduced into plant cells at a high efficiency by coculturing the cells in a medium not containing any auxin, the efficiency of callus induction from immature embryos is enhanced by centrifugation treatment, and, as a result, the transformation efficiency notably increases.

chloro-3-indolyl-β-D-glucuronic acid (X-gluc) and 20% methanol. After treatment at 37° C. for 24 hours, the expression of GUS gene in the excised root was investigated. Furthermore, the T1 plant body was placed on a regeneration medium (Harwood et al. (2008: Non-Patent Literature 11)) containing 30 mg/L of hygromycin and 5 µM $CuSO_4$ and were cultured at 25° C. in the light for about 10 days to investigate hygromycin resistance.

Results and Discussion

All T1 plants showing the expression of GUS in their roots showed hygromycin resistance (Table 5). All T1 plants not showing the expression of GUS in their roots changed into

TABLE 4

Comparison of transformation efficiency between conventional coculture medium containing dicamba and coculture medium containing 1/10 diluted MS inorganic salts (tested bacterial strain: EHA101/pIG121Hm)

| Test group | Centrifugal treatment | Number of immature embryos tested (a) | Number of divided sections | Number of sections given hygromycin-resistant regenerated plants | Number of sections given hygromycin-resistant and GUS-positive rgenerated plants | Number of immature embryos given hygromycin-resistant and GUS-positive regenerated plants (b) | Transformation efficiency (b/a: %) |
|---|---|---|---|---|---|---|---|
| 1 | — | 10 | 195 | 9 | 7 | 3 | 30.0 |
| 2 | before | 10 | 158 | 0 | 0 | 0 | 0.0 |
| 3 | after | 10 | 194 | 4 | 3 | 2 | 20.0 |
| 4 | — | 10 | 167 | 0 | 0 | 0 | 0.0 |
| 5 | before | 10 | 202 | 26 | 23 | 9 | 90.0 |
| 6 | after | 10 | 217 | 43 | 43 | 10 | 100.0 |
| 7 | after | 10 | 220 | 32 | 27 | 8 | 80.0 | before: before inoculation with *Agrobacterium*,
after: after coculture

Example 8

Genetic Analysis of Transgene in Selfed Progeny of Transformant

Two independent transformed plants, which were hygromycin-resistant and GUS-positive, obtained from different immature embryos of test group (6) in Example 6 were cultivated in a greenhouse. Immature embryos of 1.5 to 2.0 mm were aseptically collected from the resulting immature seeds. The immature embryos were placed on a regeneration medium (Harwood et al. (2008: Non-Patent Literature 11)) containing 5 µM $CuSO_4$ and were cultured at 25° C. in the light for about 2 weeks. An excised part of the root of the resulting selfed progeny (T1) plant body was immersed in a phosphate buffer solution containing 1.0 mM 5-bromo-4- brown and died in a regeneration medium containing 30 mg/L of hygromycin (Table 5). The same results were obtained in two transformation systems. The ratio of the number of transgene-expressing individuals to the number of transgene-non-expressing individuals agreed with a predicted value 3:1 of one factor segregation (Table 5). This result clearly shows that T-DNA containing a GUS gene and a hygromycin resistance gene is incorporated into the barley genome through an *Agrobacterium* strain EHA101/pIG121Hm and is inheritable to self-propagating subsequent generation in accordance with Mendel's laws.

TABLE 5

Expression analysis of transgene in the selfed progeny of barley transformant prepared using *Agrobacterium* EHA101 (pIG121Hm)

| T0 transformant system | Number of immature embryo tested | Number of germinated and rooted plants | Number of hygromycin-resistant plants of which excised root is GUS-positive | Number of hygromycin-resistant plants of which excised root is GUS-negative | Chi-square test value |
|---|---|---|---|---|---|
| GP121-104 | 40 | 39 | 32 | 7 | 1.03 (3:1) |
| GP121-111 | 35 | 35 | 27 | 8 | 0.09 (3:1) |

The invention claimed is:

1. A method of gene introduction into an immature embryonic tissue of a *Hordeum* plant, the method comprising the steps of:

(i) coculture step by inoculating the tissue with *Agrobacterium* and coculturing the tissue in the presence of the *Agrobacterium* in a coculture medium satisfying at least one of the following conditions a) to c):
  a) containing an antiauxin;
  b) containing a cytokinin; and
  c) containing an antiauxin, and containing a phenoxy auxin in an amount of less than 2 μM and/or a benzoic auxin in an amount of less than 5 μM, or not containing any phenoxy auxin and/or benzoic auxin, and
(ii) a step of subjecting the tissue to a centrifugation treatment and/or a pressurization treatment before the inoculation with *Agrobacterium*, during the coculture step, and/or after the coculture step.

2. A method of producing a transformed *Hordeum* plant, the method comprising the steps of:
  (i) coculture step by inoculating a barley immature embryonic tissue with *Agrobacterium* and coculturing the tissue in the presence of the *Agrobacterium* in a coculture medium satisfying at least one of the following conditions a) to c):
    a) containing an antiauxin;
    b) containing a cytokinin; and
    c) containing an antiauxin, and containing a phenoxy auxin in an amount of less than 2 μM and/or a benzoic auxin in an amount of less than 5 μM, or not containing any phenoxy auxin and/or benzoic auxin;
  (ii) a step of subjecting the tissue to a centrifugation treatment and/or a pressurization treatment before the inoculation with *Agrobacterium*, during the coculture step, and/or after the coculture step;
  (iii) resting step by culturing the tissue in a resting medium; and
  (iv) regeneration step by regenerating the tissue in a regeneration medium.

3. The method according to claim 2, wherein the resting step starts within 6 to 36 hours from the beginning of the coculture step.

4. The method according to claim 3, wherein the resting step starts within 12 to 24 hours from the beginning of the coculture step.

5. The method according to claim 2, wherein the coculture step finishes and the resting step starts within 6 to 36 hours after the isolation of the immature embryo.

6. The method according to claim 5, wherein the coculture step finishes and the resting step starts within 12 to 24 hours after the isolation of the immature embryo.

7. The method according to claim 1 or claim 2, further comprising the step of physically and/or chemically damaging one or more portions selected from a radicle, a plumule, and an embryonic axis of the immature embryonic tissue before the inoculation of the immature embryonic tissue with *Agrobacterium*, during the coculture step, and/or after the coculture step.

8. The method according to claim 1 or claim 2, wherein the immature embryonic tissue is cultured in the coculture step in such a manner that the scutellum side faces upward and the embryonic axis side is in contact with the coculture medium.

9. The method according to claim 1 or claim 2, further comprising at least one of the following treatments for transformation efficiency enhancement
  a) a thermal treatment;
  b) addition of silver nitrate to the coculture medium; and
  c) inoculation with *Agrobacterium* in the presence of a powder.

10. The method according to claim 1 or claim 2, further comprising the step of selection with a drug between the resting step (iii) and the regenerating step (iv).

11. The method according to claim 1 or claim 2, wherein the resting medium in the step (iii) and/or a selection medium in the step of selection with a drug contains a plant growth regulator.

12. The method according to claim 1 or claim 2, wherein the *Agrobacterium* is a bacterium selected from the group consisting of LBA4404, EHA101, EHA105, AGL0, AGL1, and C58C1.

13. The method according to claim 1 or claim 2, wherein the *Hordeum* plant is barley (*H. vulgare*).

* * * * *